(12) United States Patent
Abdulhameed et al.

(10) Patent No.: US 11,371,097 B2
(45) Date of Patent: Jun. 28, 2022

(54) ARTICLES FOR DIAGNOSIS OF LIVER FIBROSIS

(71) Applicant: THE GOVERNMENT OF THE UNITED STATES, as represented by THE SECRETARY OF THE ARMY, Fort Detrick, MD (US)

(72) Inventors: Mohamed Diwan M. Abdulhameed, Frederick, MD (US); Gregory J. Tawa, Doylestown, PA (US); Danielle L. Ippolito, Frederick, MD (US); John A. Lewis, Greencastle, PA (US); Sven Anders Wallqvist, Frederick, MD (US); Jonathan D. Stallings, Frederick, MD (US); Matthew G. Permenter, Knoxville, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 612 days.

(21) Appl. No.: 15/547,168

(22) PCT Filed: Jan. 29, 2016

(86) PCT No.: PCT/US2016/015505
§ 371 (c)(1),
(2) Date: Jul. 28, 2017

(87) PCT Pub. No.: WO2017/082943
PCT Pub. Date: May 18, 2017

(65) Prior Publication Data
US 2018/0023140 A1  Jan. 25, 2018

Related U.S. Application Data

(60) Provisional application No. 62/110,058, filed on Jan. 30, 2015.

(51) Int. Cl.
*C12Q 1/6883* (2018.01)
*C12Q 1/68* (2018.01)
*G01N 33/68* (2006.01)
*G01N 33/50* (2006.01)

(52) U.S. Cl.
CPC ............ *C12Q 1/6883* (2013.01); *C12Q 1/68* (2013.01); *G01N 33/5014* (2013.01);
(Continued)

(58) Field of Classification Search
CPC .. C12Q 1/68; C12Q 1/6883; C12Q 2600/106; C12Q 2600/118; C12Q 2600/136;
(Continued)

(56) References Cited

U.S. PATENT DOCUMENTS

2013/0323720 A1  12/2013  Watelet et al.
2015/0045247 A1  2/2015  Pottier et al.

OTHER PUBLICATIONS

Affymetrix (GeneChip® Human Transcriptome Array 2.0 datasheet, 2013) (Year: 2013).*

(Continued)

*Primary Examiner* — Jeremy C Flinders
(74) *Attorney, Agent, or Firm* — Leigh Callander; OSJA, USAMRDC

(57) ABSTRACT

Disclosed are methods and articles (e.g., gene arrays or antibodies) for determining the progression or regression of liver fibrosis, for the diagnosis of liver disease, and for screening compounds for hepatotoxicity and efficacy against liver fibrosis. Related therapeutic methods also are disclosed.

20 Claims, 15 Drawing Sheets

(52) U.S. Cl.
CPC ... *G01N 33/6893* (2013.01); *C12Q 2600/106* (2013.01); *C12Q 2600/112* (2013.01); *C12Q 2600/118* (2013.01); *C12Q 2600/136* (2013.01); *C12Q 2600/142* (2013.01); *C12Q 2600/158* (2013.01); *G01N 2800/085* (2013.01); *G01N 2800/56* (2013.01)

(58) Field of Classification Search
CPC ........ C12Q 2600/142; C12Q 2600/158; G01N 33/5014; G01N 33/6893; G01N 2800/085; G01N 2800/56
See application file for complete search history.

(56) References Cited

OTHER PUBLICATIONS

Bulla et al. (Genomics, 2010, 96:323-332) (Year: 2010).*

Affymetrix (GeneChip® Rat Genome 230 Arrays datasheet, 2004) (Year: 2004).*

Ippolito et al., "Gene expression patterns Associated with histopathology in toxic liver fibrosis", Toxicol Sci., Sep. 22, 2015, vol. 149, No. 1, pp. 67-88.

Staten et al., "Multiplex transcriptional analysis of paraffin-embedded liver needle biopsy from patients with liver fibrosis", Fibrogenesis Tissue Repair, Dec. 27, 2017, vol. 5, No. 1, pp. 1-7.

Abdulhameed et al., "Systems level analysis and identification of pathways and networks associated with liver fibrosis", PLoS One, 2014, vol. 9, No. 11, pp. 1-14.

Robinson et al., "A comparison of Affymetrix gene expression arrays", BMC Bioinformatics, Biomed Central, London, GB, vol. 8, No. 1, Nov. 15, 2007 (Nov. 15, 2007), p. 449, XP021031592.

Willyard, "Expanded human gene tally reignites debate," Nature, vol. 558, Jun. 21, 2018, pp. 354-355.

Pilcher, "Rat genome unveiled," https://www.nature.com/articles/news040329-11#citeas, Nature, 2004, 5 pages.

* cited by examiner

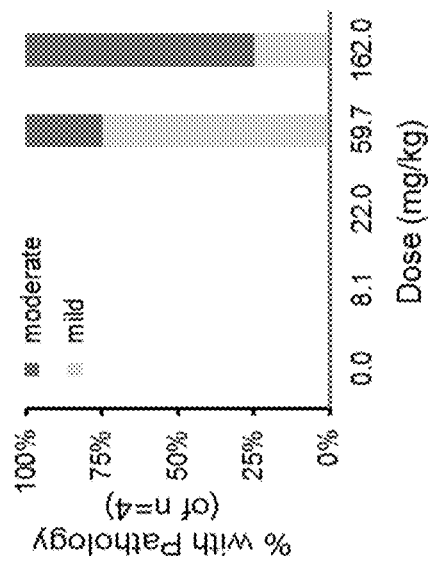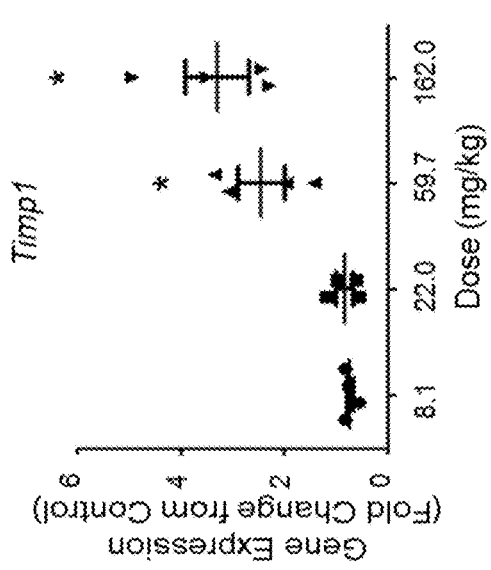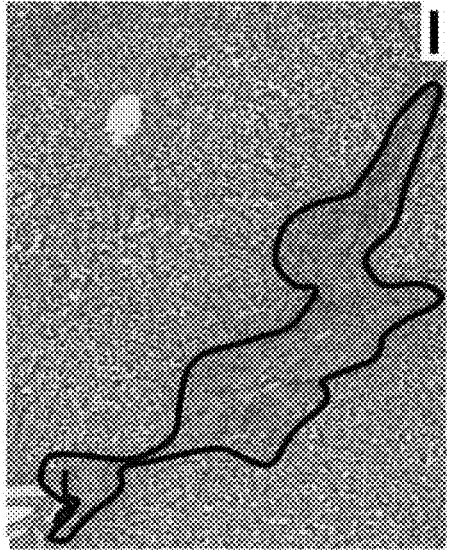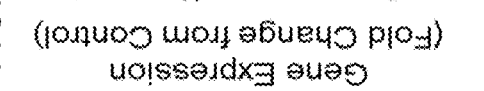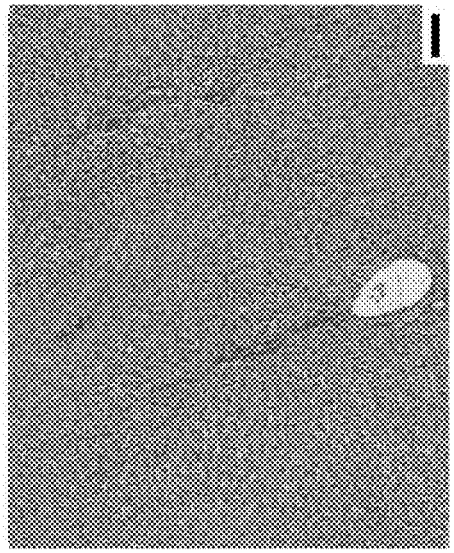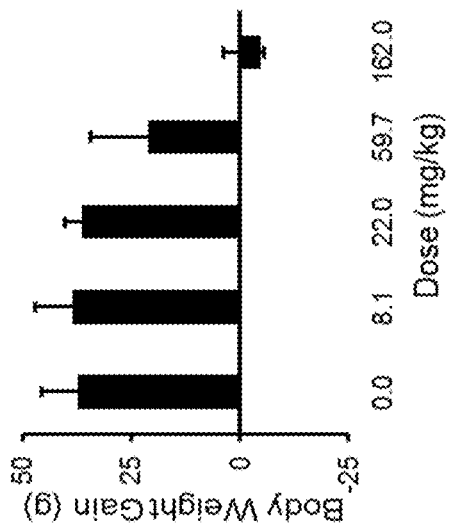

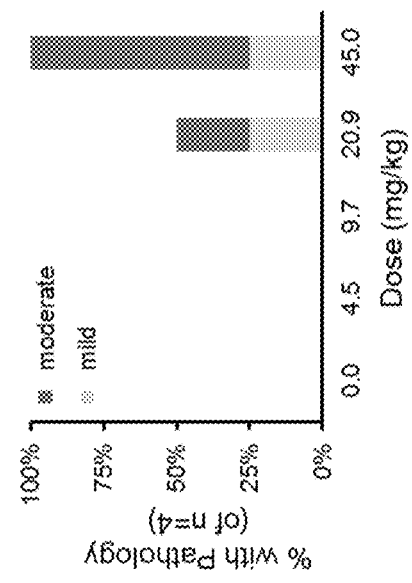
FIG. 2A
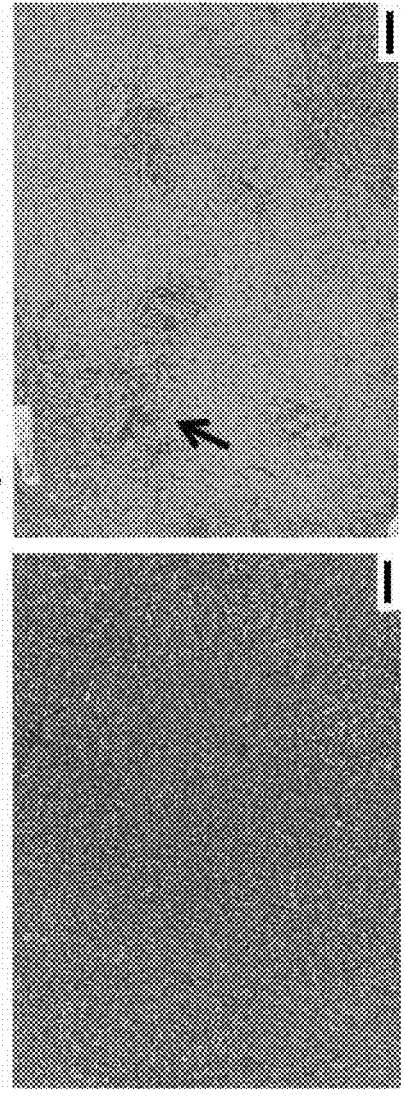
FIG. 2B
FIG. 2C
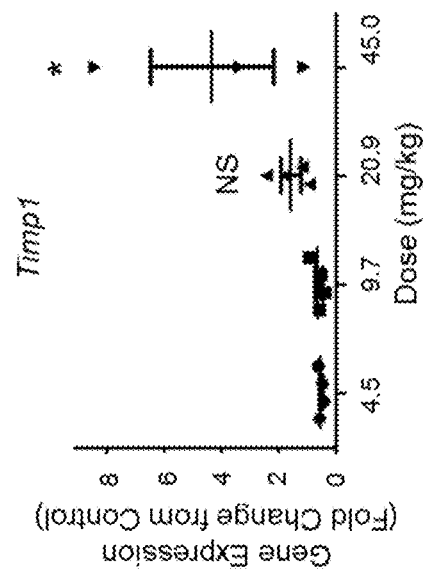
FIG. 2D
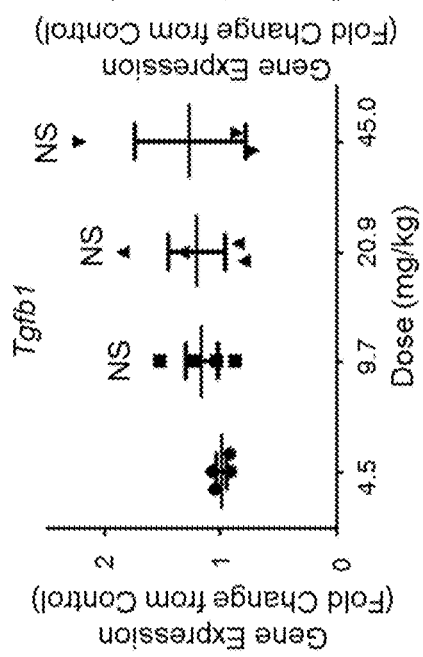
FIG. 2E
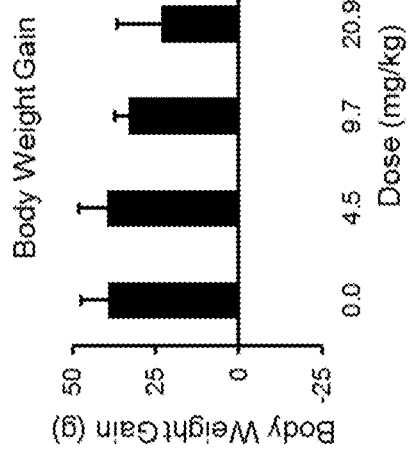
FIG. 2F

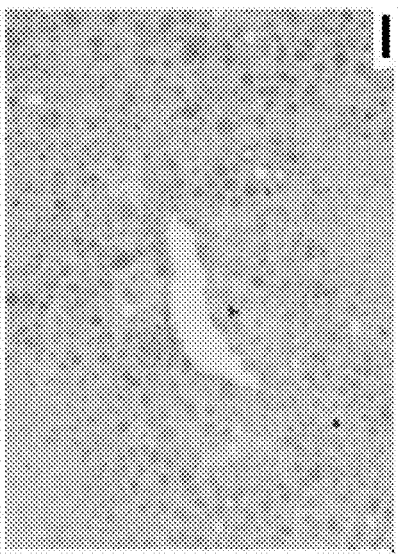 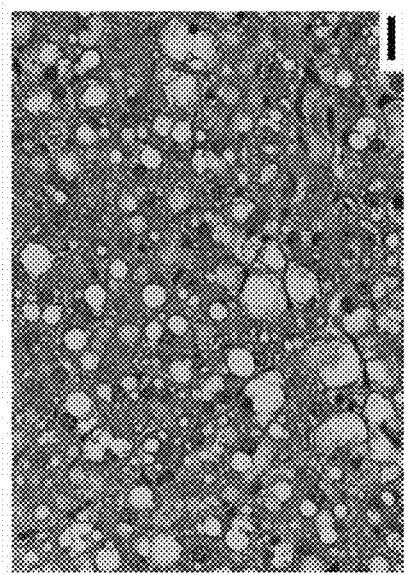 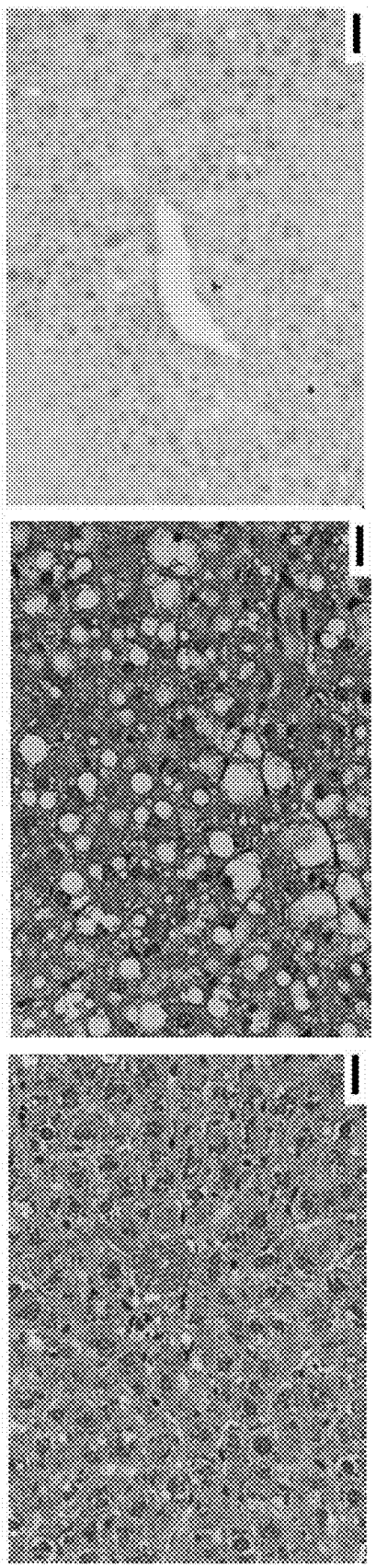
FIG. 3A  FIG. 3B  FIG. 3C
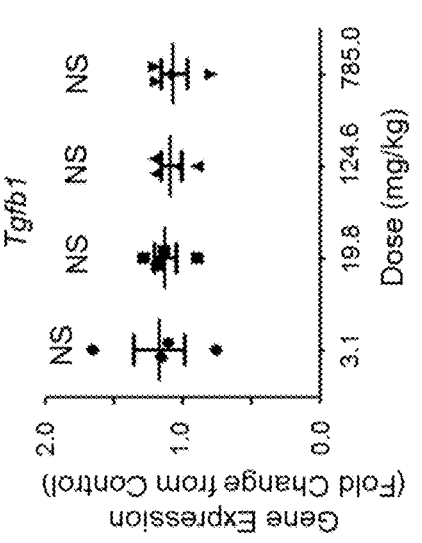
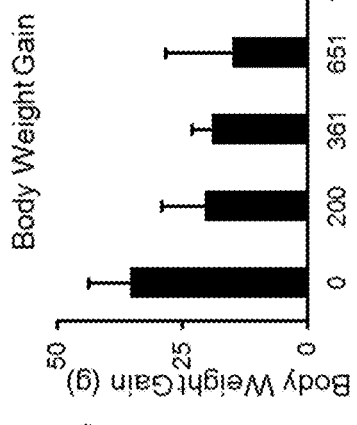
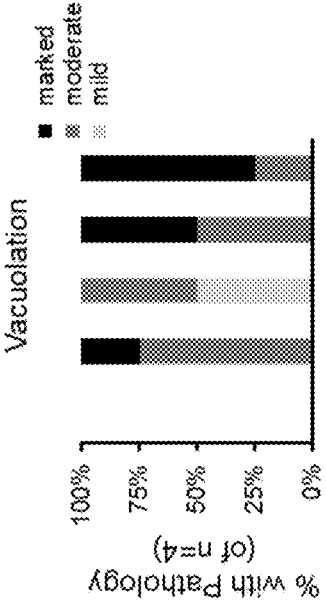
FIG. 3D  FIG. 3E  FIG. 3F

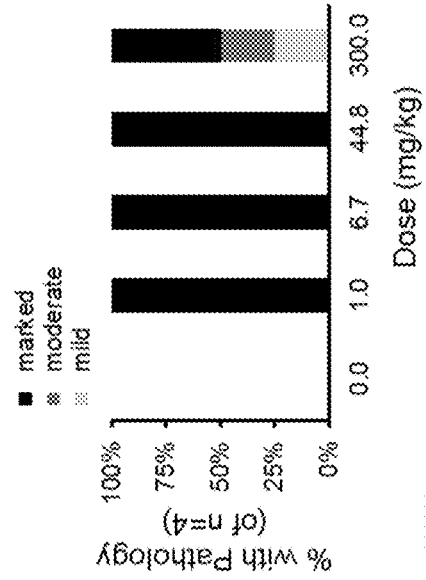
FIG. 4A
Control, 40x
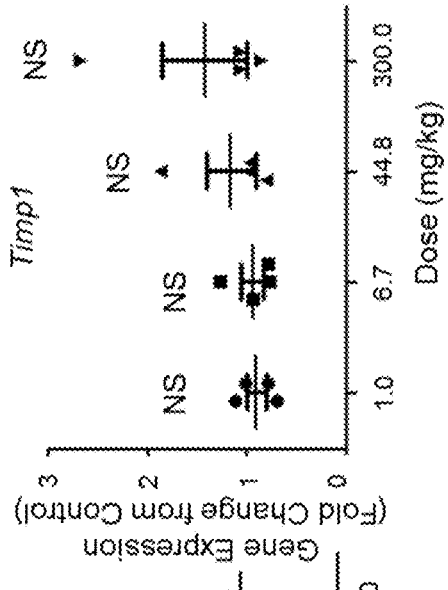
FIG. 4B
Dexamethasone, 40x
FIG. 4C
Cytoplasmic Alteration
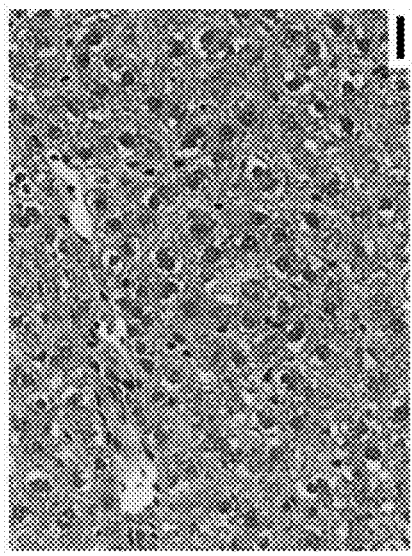
FIG. 4D
Body Weight Gain
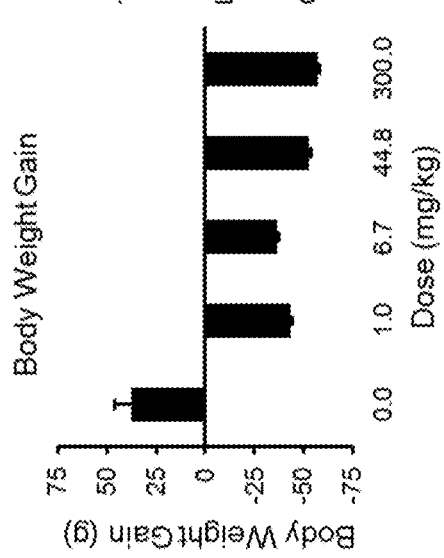
FIG. 4E
Tgfb1
FIG. 4F
Timp1

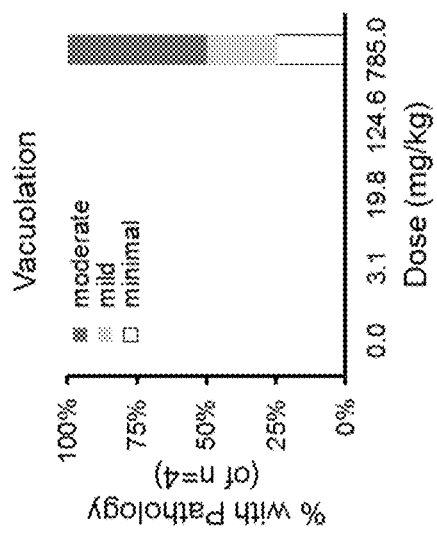
FIG. 5A Control, 40x
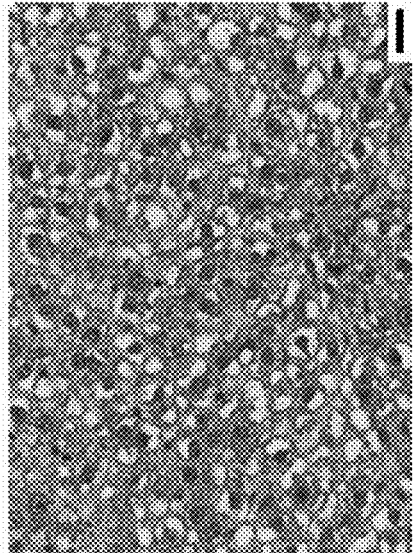
FIG. 5B Bromobenzene, 40x
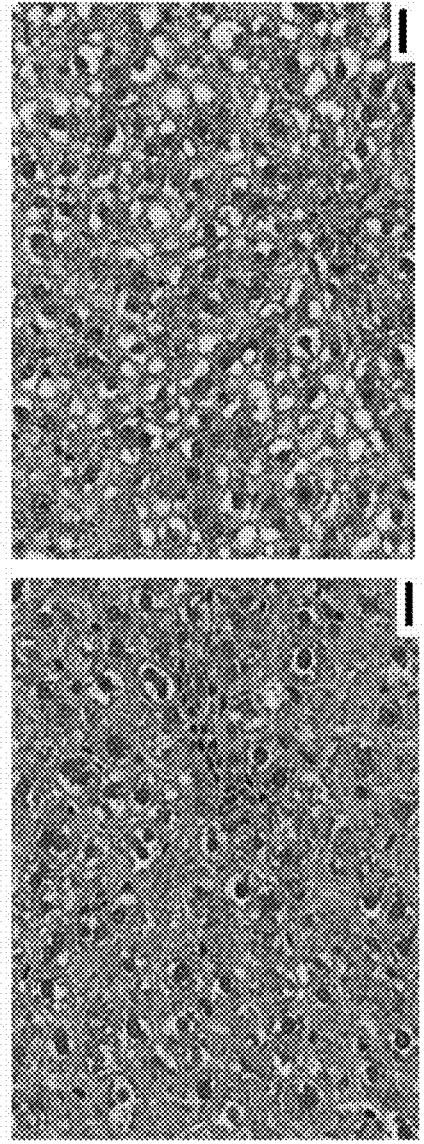
FIG. 5C
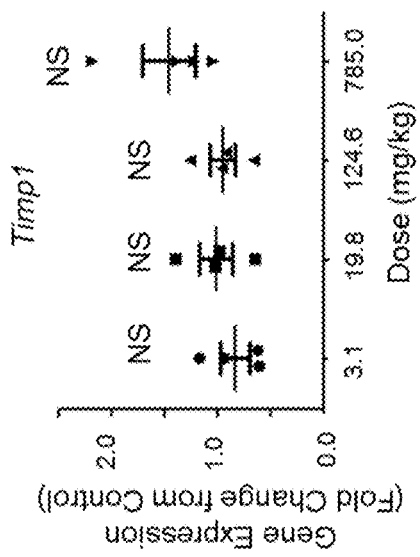
FIG. 5D
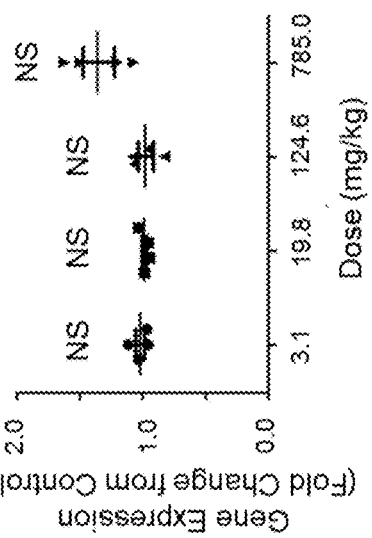
FIG. 5E
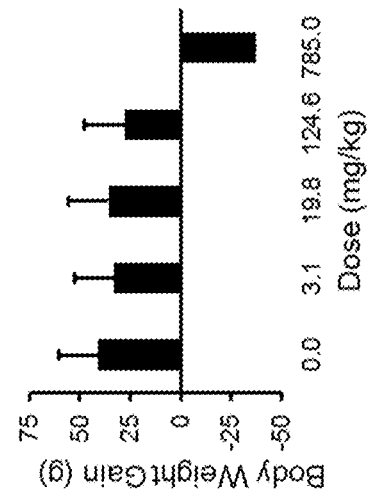
FIG. 5F 4,4'-Methylenedianiline, 40x Carbon Tetrachloride, 40x Control, 40x Control

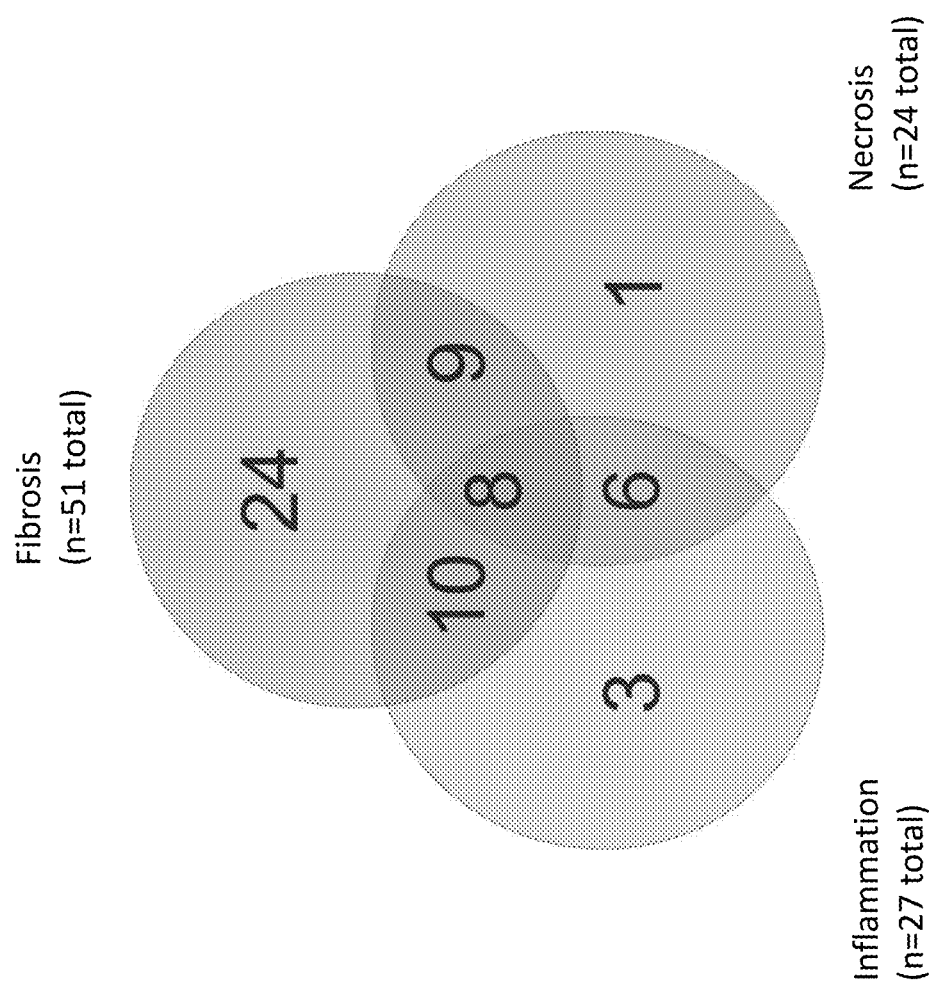

US 11,371,097 B2

ARTICLES FOR DIAGNOSIS OF LIVER FIBROSIS

RELATED APPLICATIONS

This application is a U.S. National Stage Application under 35 U.S.C. § 371 of International Application No. PCT/US2016/015505 filed Jan. 29, 2016, which claims priority to U.S. Provisional Application No. 62/110,058 filed Jan. 30, 2015, the entire contents of which are incorporated by reference herewith.

FEDERALLY SPONSORED RESEARCH OR DEVELOPMENT

This invention was made with government support and the government has certain rights in the invention.

BACKGROUND OF THE INVENTION

Disclosed herein are methods and articles (e.g., gene arrays or antibodies or qPCR or RNA sequencing) for determining the progression or regression of liver fibrosis, for the diagnosis of liver disease, and for screening compounds for hepatotoxicity and efficacy against liver fibrosis. Related therapeutic methods also are disclosed.

Liver fibrosis is the characteristic pathologic feature of most chronic liver diseases. It is marked by chronic inflammation and excessive accumulation of extracellular matrix (ECM) components. Liver fibrosis is a progressive disease that leads to cirrhosis, portal hypertension, and ultimately results in liver failure. It can also result in hepatocellular carcinoma.

Liver fibrosis is caused by diverse factors such as hepatitis B and hepatitis C virus infection, alcoholism (alcoholic steatohepatitis), obesity (non-alcoholic steatohepatitis), and exposure to toxic chemicals. Such chronic liver diseases are fast becoming a major health problem that affects millions of people worldwide. In 2010, nearly one million deaths globally were attributed to liver cirrhosis. It is estimated that approximately 370 million and 130 million people are infected with hepatitis B and C virus respectively. Every year, nearly 6000 liver transplantations are performed each year in the U.S. and Europe. Estimated costs of cirrhosis and chronic liver disease in the U.S. were approximately $2.5 billion (direct) and $10.6 billion (indirect) in 2004. Since the factors contributing to chronic liver disease are growing in epidemic proportion, this burden is expected to rise significantly over the next 20 years. Currently, there are no approved drugs for the treatment of liver fibrosis.

Liver biopsy is the current gold standard for determining the presence of liver fibrosis. However, liver biopsy is an invasive procedure and requires hospitalization. The use of liver biopsy has a number of limitations such as sampling issues and intra/inter-observer variations. One of the clinically used non-invasive diagnostic tests for liver injury is the FibroSure panel, which is based on a predictive algorithm incorporating age, gender, and blood concentrations of the analytes a2-macroglobulin, haptoglobulin, bilirubin, and apolipoprotein A. Although the panel correlates well with late-stage fibrosis diagnosed by liver biopsy, it lacks sensitivity and specificity as an early (stage 1-2) diagnostic indicator.

There also is a need for improved methodologies for identifying the hepatotoxicity of potential drug candidates. Hepatotoxicity is a common form of toxicity encountered in drug development, and is responsible for the withdrawal of many drugs from the market. Earlier identification of such potential toxic compounds will help to improve the drug discovery process and will save significant amounts of cost and time. For example, the ability to identify compounds that have the propensity to cause liver fibrosis during pre-clinical development could improve the drug discovery process and provide potential savings in drug development. Speaking generally, the use of better biomarkers in pre-clinical development could reduce the average drug development costs by >$100 million.

BRIEF SUMMARY OF THE INVENTION

Disclosed herein are methods and articles for determining the progression or regression of liver fibrosis in a mammalian subject. In some embodiments, the methods comprise detecting differential expression of at least twenty-five genes listed in Table 4 and selected from the list below, or an ortholog thereof corresponding to the mammalian subject. In particular, the methods comprise detecting differential expression of at least twenty-five genes selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof corresponding to the mammalian subject, in a biological sample from the subject. In some embodiments, the methods comprise detecting differential expression of at least 30, at least 35, at least 40, at least 45, or at least 50 genes set forth in Table 4, or corresponding mammalian orthologs thereof.

In some embodiments, the methods comprise detecting differential expression of at least 25, at least 30, at least 35, at least 40, at least 45, or at least 50 proteins, peptides and/or amino acids which is encoded by a gene set forth in Table 4, or corresponding mammalian orthologs thereof. In yet another embodiment the proteins, peptides and/or amino acids can be detected in plasma or serum.

In some embodiments, the methods comprise detecting differential expression of at least 25, at least 30, at least 35, at least 40, at least 45, or at least 50 gene regulators which correspond to the gene set forth in Table 4, or corresponding mammalian orthologs thereof. In yet another embodiment the gene regulators can be detected in plasma or serum.

In some embodiments, the subject is a rat, mouse, guinea pig, pig, rabbit, dog, cat, cow, horse, or human. In some embodiments, the subject is a human.

Also disclosed are methods for detecting early stage liver disease in a mammalian subject, comprising assaying a biological sample from the subject for differential expression of at least 25 genes selected from Table 4 and selected from the list above and corresponding mammalian orthologs thereof wherein the differential expression of the at least 25 genes is indicative of early stage liver disease in the subject. In some embodiments, the method involves assaying the biological sample for differential expression of at least at least 30, at least 35, at least 40, at least 45, or at least 50 of the genes set forth in Table 4. In some embodiments, the methods comprise detecting differential expression of at least 25, at least 30, at least 35, at least 40, at least 45, or at least 50 proteins, peptides and/or amino acids which is encoded by a gene set forth in Table 4, or corresponding mammalian orthologs thereof. In some embodiments, the methods comprise detecting differential expression of at least 25, at least 30, at least 35, at least 40, at least 45, or at least 50 regulators which correspond to a gene set forth in Table 4, or corresponding mammalian orthologs thereof.

In some embodiments, differential expression of each of the at least 25 genes by an amount of at least 0.5 fold ($\log_2$) as compared to a control is indicative of early stage liver disease. In some embodiments, differential expression of at least one of the at least 25 genes by an amount of at least 0.6, 0.7, 0.8, 0.9, 1.0, 1.1, 1.2, 1.3, 1.4 or 1.5, 2.0, 2.5, or 3 fold ($\log_2$) as compared to a control is indicative of early stage liver disease.

In some embodiments, differential expression of each of at least 25 proteins, peptides and/or amino acids by an amount of at least 0.5 fold ($\log_2$) as compared to a control is indicative of early stage liver disease. In some embodiments, differential expression of at least one of the at least 25 proteins, peptides and/or amino acids by an amount of at least 0.6, 0.7, 0.8, 0.9, 1.0, 1.1, 1.2, 1.3, 1.4 or 1.5, 2.0, 2.5, or 3 fold ($\log_2$) as compared to a control is indicative of early stage liver disease.

In some embodiments, differential expression of each of at least 25 gene regulators by an amount of at least 0.5 fold ($\log_2$) as compared to a control is indicative of early stage liver disease. In some embodiments, differential expression of at least one of the at least 25 gene regulators by an amount of at least 0.6, 0.7, 0.8, 0.9, 1.0, 1.1, 1.2, 1.3, 1.4 or 1.5, 2.0, 2.5, or 3 fold ($\log_2$) as compared to a control is indicative of early stage liver disease.

In some embodiments, increased expression of at least one gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ce12; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof.

In some embodiments, increased expression of at least one protein, peptide or amino acid which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ce12; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ce12; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof.

In some embodiments, increased expression of at least one gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Cc/2; Serpine1; Cyba; Fam105a; Cxcl1; Vim; C1qb, Pcolce; Fxyd5; Arpc1b; S100a6; Plau; Itgal; Plod2; Ctgf Col1a2; Igfbp2, and mammalian orthologs thereof.

In some embodiments, increased expression of at least one protein, peptide or amino acids which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Cc/2; Serpine1; Cyba; Fam105a; Cxcl1; Vim; C1qb; Pcolce; Fxyd5; Arpc1b; S100a6; Plau; Itgal; Plod2; Ctgf Col1a2; Igfbp2, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Cc/2; Serpine1; Cyba; Fam105a; Cxcl1; Vim; C1qb; Pcolce; Fxyd5; Arpc1b; S100a6; Plau; Itgal; Plod2; Ctgf Col1a2; Igfbp2, and mammalian orthologs thereof.

In some embodiments, increased expression of at least one gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and mammalian orthologs thereof.

In some embodiments, increased expression of at least one protein, peptide or amino acids which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and mammalian orthologs thereof.

In some embodiments, decreased expression of at least one gene selected from the following group is indicative of early stage liver disease: Cyp2c11; Igfbp3; Cxcl12; Angptl3; Igfals; Tgfb1; Vtn; Vhl; and mammalian orthologs thereof.

In some embodiments, decreased expression of at least one protein, peptide or amino acid which is encoded by a gene selected from the following group is indicative of early stage liver disease: Cyp2c11; Igfbp3; Cxcl12; Angptl3; Igfals; Tgfb1; Vtn; Vhl; and mammalian orthologs thereof.

In some embodiments, decreased expression of at least one gene regulator which corresponds to a gene selected from the following group is indicative of early stage liver disease: Cyp2c11; Igfbp3; Cxcl12; Angptl3; Igfals; Tgfb1; Vtn; Vhl; and mammalian orthologs thereof.

In some embodiments, the methods disclosed herein detect early stage liver disease with at a sensitivity of at least 70%, 75%, 80%, 85%, 90%, or at least 95% sensitivity. In some embodiments, the methods disclosed herein detect early stage liver disease with at least 70%, 75%, 80%, 85%, 90%, or at least 95% specificity.

In accordance with any of the embodiments described herein, the biological sample may be selected from blood, plasma, serum, urine, or a liver biopsy.

In accordance with any of the embodiments described herein, differential expression may be determined by quantification of the levels of the proteins encoded by the genes, such as by Western blotting, ELISA or mass spectrometry. Additionally or alternatively, differential expression may be determined by quantification of corresponding mRNA, cDNA or miRNA levels, such as by using an oligonucleotide array comprising probes specific to mRNA, cDNA or miRNA corresponding to each of the twenty-five genes.

In accordance with other embodiments, there are disclosed methods of identifying whether a compound increases or decreases the differential expression of at least one gene selected from the following list, comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Co14a1; Sod2; Cyp2c11; Igfbp3; Cxcl12; Angptl3; Igfals; Tgfb1; Vtn; Vhi, Dsc2; Fam102b; Fam105a; Gpnmb; Pcolce; RT1-Da; RT1-DMa; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof, contacting the cell with a test compound; and determining whether the differential expression of the at least one gene is increased or decreased in the presence of the test compound.

In accordance with other embodiments, there are disclosed methods of identifying whether a compound increases or decreases the differential expression of at least one protein, peptide or amino acid which is encoded by a gene selected from the following list, comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Co14a1; Sod2; Cyp2c11; Igfbp3; Cxcl12; Angptl3; Igfals; Tgfb1; Vtn; Vhi, Dsc2; Fam102b; Fam105a; Gpnmb; Pcolce; RT1-Da; RT1-DMa; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof, contacting the cell with a test compound; and determining whether the differential expression of the at least one gene is increased or decreased in the presence of the test compound.

In accordance with other embodiments, there are disclosed methods of identifying whether a compound increases or decreases the differential expression of at least one gene regulator which corresponds to a gene selected from the following list, comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Co14a1; Sod2; Cyp2c11; Igfbp3; Cxcl12; Angptl3; Igfals; Tgfb1; Vtn; Vhi, Dsc2; Fam102b; Fam105a; Gpnmb; Pcolce; RT1-Da; RT1-DMa; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof, contacting the cell with a test compound; and determining whether the differential expression of the at least one gene is increased or decreased in the presence of the test compound.

In accordance with other embodiments, there are disclosed methods of treating liver disease, comprising administering to a mammalian subject in need thereof, a therapeutically effective amount of a compound identified by the disclosed methods to decrease expression of a gene selected from the group consisting of Lcn2; Gpnmb; Lgals3; S100a11; Anxa2; Lbp; Col1a1; Cxcl16; Timp1; Plat; RT1-DMa; Cd9; Lgals1; Tagin2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof and/or to differentially express a gene selected from the group consisting of Fbn1; Col4a1; Sod2; Cyp2c11; Igfbp3; Cxcl12; Angptl3; Igfals; Tgfb1; Vtn; Vhl; Dsc2; Fam102b; Fam105a; Gpnmb; Pcolce; RT1-Da; RT1-DMA; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof.

In accordance with other embodiments, there are disclosed methods of treating liver disease, comprising administering to a mammalian subject in need thereof, a therapeutically effective amount of a compound identified by the disclosed methods to decrease expression of a protein, peptide or amino acid which is encoded by a gene selected from the group consisting of Lcn2; Gpnmb; Lgals3; S100a11; Anxa2; Lbp; Col1a1; Cxcl16; Timp1; Plat; RT1-DMa; Cd9; Lgals1; Tagin2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof and/or to differentially express a gene selected from the group consisting of Fbn1; Col4a1; Sod2; Cyp2c11; Igfbp3; Cxcl12; Angptl3; Igfals; Tgfb1; Vtn; Vhl; Dsc2; Fam102b; Fam105a; Gpnmb; Pcolce; RT1-Da; RT1-DMA; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof.

In accordance with other embodiments, there are disclosed methods of treating liver disease, comprising administering to a mammalian subject in need thereof, a therapeutically effective amount of a compound identified by the disclosed methods to decrease expression of a gene regulator which corresponds to a gene selected from the group consisting of Lcn2; Gpnmb; Lgals3; S100a11; Anxa2; Lbp; Col1a1; Cxcl16; Timp1; Plat; RT1-DMa; Cd9; Lgals1; Tagin2: RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; S/c25a24, and mammalian orthologs thereof and/or to differentially express a gene selected from the group consisting of Fbn1; Col4a1; Sod2; Cyp2c11; Igfbp3; Cxcl12; Angptl3; Igfals; Tgfb1; Vtn; Vhl; Dsc2; Fam102b; Fam105a; Gpnmb; Pcolce; RT1-Da; RT1-DMA; Slc25a24; Sod2; Taln2; Arpc1b; Angptl3; Anxa2; Cd53; Cd9; Cp; C1qb; Fxyd5; Igfbp1; Igfbp2; Igfbp3; Igfals; Lamc2; Lgals1; Lgals3 bp; Lrp1; Plod2; Pkm; S100a11; S100a6; Serpine1; Serping1; Vim, and mammalian orthologs thereof.

In accordance with other embodiments, there are disclosed arrays comprising at least twenty-five target oligonucleotides immobilized on a substrate, wherein the target oligonucleotide each comprise a sequence that is specifically hybridizable to mRNA, cDNA or miRNA corresponding to one of the at least twenty-five genes from Table 4, and mammalian orthologs thereof, such that the array comprises at least one target oligonucleotide specifically hybridizable to each of the at least twenty-five genes. In some embodiments, the target oligonucleotides are labelled with a detectable label. In some embodiments, the target oligonucleotides comprise cDNA-specific sequences, wherein the cDNA-specific sequences comprises at least one nucleotide that differs from the corresponding genomic DNA. In some embodiments, there is provided an apparatus comprising an array as disclosed herein.

In accordance with other embodiments, there are disclosed kits for the diagnosis of liver disease, comprising at least twenty-five detectably labelled oligonucleotides, wherein the oligonucleotides comprise a sequence that is specifically hybridizable to mRNA, cDNA or miRNA corresponding to at least twenty-five separate genes from Table 4, and mammalian orthologs thereof, such that the kit comprises at least one detectably labelled oligonucleotide specifically hybridizable to each of the at least twenty-five genes.

In accordance with other embodiments, there are disclosed kits for the diagnosis of liver disease, comprising at least twenty-five antibodies, or antigen binding fragments thereof, each capable of binding to one of at least twenty-five separate proteins encoded by genes from Table 4, and mammalian orthologs thereof, such that the kit comprises at least one antibody or fragment thereof that specifically binds to each of the proteins encoded by each of the at least twenty-five genes.

BRIEF DESCRIPTION OF SEVERAL VIEWS OF THE DRAWINGS

FIGS. 1A-1F exemplify dose-dependent liver pathology and pre-fibrotic gene expression after 4,4'-methylenedianiline. Livers from rats administered 0, 8.1, 22, 59.7, and 162 mg/kg 4,4'-methylenedianiline per day for five days (n=4 per group) were stained with hematoxylin and eosin and scored for histopathological evidence of bile duct hyperplasia and fibrosis.

FIGS. 1A and 1B are representative images from a control liver (FIG. 1A) and the liver of a 4,4'-methylenedianiline-treated rat (FIG. 1B) at 10× magnification. FIG. 1C depicts the combined results for histopathological scores as percent of animals with pathology showing a dose-dependent increase in severe pathology. FIG. 1D exemplifies a decrease in body weight gain over the five experimental dosing days. FIGS. 1E and 1F depict dose-dependent increases in gene expression for the pre-fibrosis indicators Tgfb1 (FIG. 1E) and Timp1 (FIG. 1F) by qPCR. NS, not significant; *, $p<0.05$ by one sample t-test comparing to a theoretical mean of 1.0; black arrow, bile duct hyperplasia. Scale bar denotes 100 μm.

FIGS. 2A-2F exemplify dose-dependent liver pathology and pre-fibrotic gene expression in rats after exposure to allyl alcohol. Livers from rats administered 0, 4.5, 9.7, 20.9, and 45 mg/kg allyl alcohol per day for five days (n=4 per group) were stained with hematoxylin and eosin and scored for histopathological evidence of bile duct hyperplasia and fibrosis.

FIGS. 2A and 2B are representative images from a control liver (FIG. 2A) and a liver from an allyl alcohol-treated rat (FIG. 2B; 45 mg/kg) at 10× magnification. FIG. 2C depicts combined results for histopathological scores as percent of animals with pathology showing a dose-dependent increase in severe pathology. FIG. 2D exemplifies an increase in body weight gain over the five experimental dosing days. FIGS. 2E and 2F depict changes in gene expression for the pre-fibrosis indicators Tgfb1 (FIG. 2E) and Timp1 (FIG. 2F) by qPCR. NS, not significant; *, $p<0.05$ by one sample t-test comparing to a theoretical mean of 1.0; black arrow, bile duct hyperplasia. Scale bar denotes 100 μm.

FIGS. 3A-3F exemplify dose-dependent vacuolation consistent with lipid accumulation without change in prefibrotic gene expression after carbon tetrachloride exposure. Livers from rats administered 0, 200, 360.9, 651.2, and 1175 mg/kg carbon tetrachloride per day for five days (n=4 per group) were stained with hematoxylin and eosin or Oil Red 0 and scored for histopathological evidence of vacuolation.

FIGS. 3A and 3B are representative images from a control liver (FIG. 3A) and the liver of a carbon tetrachloride-treated rat (FIG. 3B; 200 mg/kg) at 40× magnification after hematoxylyn and eosin staining; scale bar, 20 μm. FIG.3C is a representative image from carbon tetrachloride-dosed animal after Oil Red 0 staining for lipid accumulation, 20× magnification; scale bar, 50 μm. FIG. 3D exemplifies combined results for histopathological scores as percent of animals with pathology showing a dose-dependent increase in severe pathology. FIG. 3E exemplifies a decrease in body weight gain over the five experimental dosing days. FIG. 3F exemplifies a change in gene expression were insignificant for the pre-fibrosis indicator Tgfb1 by qPCR. NS, not significant by one-sample t-test to a theoretical value of 1.0.

FIGS. 4A-4F exemplify dose-dependent liver pathology consistent with glycogen accumulation and lower expression of pre-fibrotic Tgfb1 gene expression after dexamethasone exposure. Livers from rats administered 0, 1, 6.7, 44.8, or 300 mg/kg dexamethasone per day for five days (n=4 per group) were stained with hematoxylin and eosin and scored for histopathological evidence of cytoplasmic alteration consistent with glycogen accumulation.

FIGS. 4A and B are representative images from a control liver (FIG. 4A) and the liver of a dexamethasone-treated rat (FIG. 4B; 300 mg/kg) at 40× magnification. FIG. 4C depicts the combined results for histopathological scores as percent of animals with pathology showing a dose-dependent increase in severe pathology. FIG. 4D exemplifies decrease in body weight gain over the five experimental dosing days. FIGS. 4E and 4F depict decreased gene expression for the fibrosis indicator Tgfb1 (FIG. 4E) and the lipid accumulation indicator Timp1 (FIG. 4F) by qPCR. NS, not significant; *, $p<0.05$ by one sample t-test comparing to a theoretical mean of 1.0. Scale bar denotes 20 μm.

FIGS. 5A-5F exemplify dose-dependent NASH liver pathology without change in prefibrotic gene expression in rats after bromobenzene exposure. Livers from rats administered 0, 3.1, 19.8, 124.6, 785 mg/kg bromobenzene per day for five days (n=4 per group) were stained with hematoxylin and eosin and scored for histopathological evidence of vacuolation.

FIGS. 5A and 5B are representative images from a control liver (FIG. 5A) and bromobenzene (FIG. 5B; 785 mg/kg) at 40× magnification. FIG. 5C depicts the combined results for histopathological scores as percent of animals with pathology showing a dose-dependent increase in severe pathology. FIG. 5D exemplifies a decrease in body weight gain over the five experimental dosing days. FIG. 5E shows a slight, statistically insignificant increase in gene expression for the pre-fibrosis indicator Tgfb1 by qPCR, and FIG. 5F shows a statistically significant increase in the lipid accumulation indicator Timp1 by qPCR. NS, not significant by one sample t-test comparing to a theoretical mean of 1.0.

FIG. 6A exemplifies bile duct in control livers; dark gray denotes normal collagen. FIG. 6B exemplifies periportal region, with increased collagen (fibrosis) and bile duct hyperplasia. 40× magnification. FIG. 6C exemplifies centrilobular vein in control animals. FIG. 6D exemplifies centrilobular collageous accumulation demonstrated by a dark gray halo rimming a centrilobular vein in carbon tetrachloride-treated animals. 40× magnification; black scale bar, 20 µm. Masson's trichrome.

FIG. 13(A) exemplifies a Venn diagram indicating genes associated with fibrosis, inflammation, and necrosis endpoints (Group 1 experimental animals) unique to fibrosis endpoint, inflammation, or necrosis.

DETAILED DESCRIPTION OF THE INVENTION

Figure 6B:
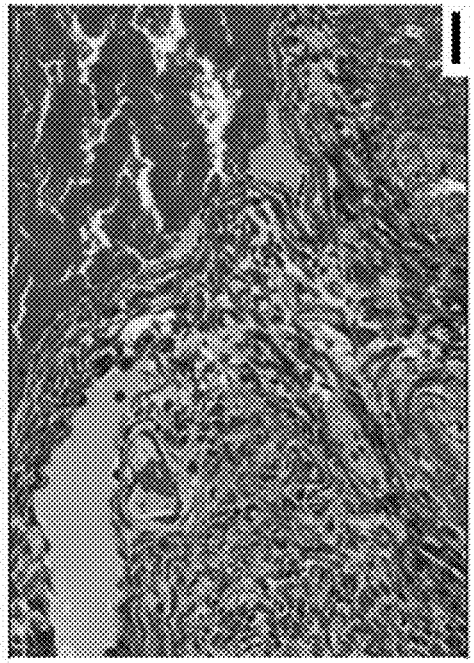
FIGS. 6A-6D exemplify periportal fibrosis in rats after five-day oral administration of 162 mg/kg/day 4,4'-methylenedianiline and pre-fibrogenic lesions in centrilobular region after 200 mg/kg/day carbon tetrachloride administration.

Disclosed herein are methods and articles (e.g., gene arrays or antibodies) for determining the progression or regression of liver fibrosis, for the diagnosis of liver disease, and for screening compounds for hepatotoxicity and efficacy against liver fibrosis. Related therapeutic methods also are disclosed. The methods and article relate to a panel of at least twenty-five genes whose differential expression is indicative of liver fibrosis, liver disease, and/or hepatotoxicity. In general, changes in gene expression levels precede the changes in tissue-level that can be observed in histopathological analysis or clinical chemistry analysis. The disclosed panel allows for earlier identification of liver fibrosis or liver disease than can be observed in other approaches, as demonstrated by the carbon-tetrachloride exposure study set forth below.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference are made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any animal, including humans. The term "mammalian subject," includes all mammalian animals, such as rat, mouse, guinea pig, pig, rabbit, dog, cat, cow, horse, and human subjects.

As used herein, the phrases "therapeutically effective amount" and "therapeutic level" mean that dosage or plasma concentration in a subject, respectively, that provides the specific pharmacological response for which the physiologically active agent is administered in a subject in need of such treatment. It is emphasized that a therapeutically effective amount or therapeutic level will not always be effective in treating the target conditions/diseases, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, the term "differential expression" refers to gene expression on the RNA/mRNA level, protein level, or both RNA/mRNA and protein levels as compared to a reference level of gene expression (control), e.g., an increased or decreased gene expression on the RNA/mRNA level, protein level, or both RNA/mRNA and protein levels. In some embodiments, the reference level of gene expression is gene expression from a normal animal or cell, lacking evidence of liver fibrosis. In some embodiments, the reference level of gene expression is gene expression from an animal or cell known to be positive for liver fibrosis. In some embodiments, the liver fibrosis can be that which accompanies either early stage or late stage liver disease.

As used herein, the terms "gene" and "gene encoding a protein" refer to any nucleic acid sequence or portion thereof with a functional role in encoding or transcribing a protein.

As used herein, the terms "mRNA" and "messenger RNA" refer to RNA molecules that convey genetic information from DNA to the ribosome, where they specify the amino acid sequence of the protein products of gene expression.

As used herein, the terms "cDNA" and "complementary DNA" refer to double-stranded DNA synthesized from a messenger RNA (mRNA) template in a reaction catalysed by the enzyme reverse transcriptase.

As used herein, the terms "miRNA" and "micro RNA" refer to a small non-coding RNA molecule found in plants, animals, and some viruses, which functions in RNA silencing and post-transcriptional regulation of gene expression.

As used herein, the term "oligonucleotide" refers to oligonucleotides that bind in a base-specific manner to a complementary strand of nucleic acid. Such oligonucleotides also include peptide nucleic acids, and other nucleic acid analogs and nucleic acid mimetics.

As used herein, the DrugMatrix database refers to a public repository of microarray data, histopathology, and clinical chemistry data from more than 3,200 drug and toxicant exposures in rats. The DrugMatrix database was analyzed to identify gene signatures related to late stage liver disease.

As used herein, "sensitivity" refers to the true positive rate. As used herein, "specificity" refers to the true negative rate.

In some embodiments, the methods and articles disclosed herein are useful for determining the progression or regression of liver fibrosis in a subject, or for assessing the presence and/or stage of progression of fibrotic injury using a liver biopsy specimen or a biological sample from the subject, with greater sensitivity and specificity than current practices (such as 100% sensitivity and 84% specificity). Further, in some embodiments, the disclosed methods can be used with non-invasively obtained biological samples (e.g., blood, serum, urine, etc.) which will aid in fibrosis diagnosis at a fraction of the cost of a liver biopsy.

Specific applications make possible the diagnosis of adverse health effects after toxic chemical injury without the need for identification or characterization of the chemical which caused the injury. Thus, instead of developing an impractical number of exposure-based assays, a single assay can diagnose adverse health effect regardless of the nature of the chemical which caused the injury.

Other specific applications pertain to the diagnosis of liver fibrosis without the need for histopathology. In specific embodiments, the methods are used in drug development, to assess hepatotoxicity of drug candidates without requiring histopathological evaluation, which is labor intensive and requires a board-certified histopathologist to properly diagnose. Current procedures can only diagnose later stages of fibrotic injury. Most molecular biology laboratories are staffed with trained veterinary pathologists with the capability to read and accurately diagnose specimens. The disclosed inventions circumvent the need for a trained, board-certified histopathologist, representing a significant cost savings by allowing researchers earlier, more accurate diagnoses without extensive histopathological training.

Other specific applications pertain to commercial products with diagnostic potential, such as handheld devices and kits for use in clinical and research settings. Integration of kits into standard drug development will aid in earlier identification of compounds with fibrotic potential and produce significant cost savings to the pharmaceutical industry.

Some embodiments of the methods and articles disclosed herein are useful for identifying drugs that may induce hepatotoxicity, and for developing drugs useful against hepatotoxicity.

Further, in some embodiments, the disclosed methods can be used for toxicity screening in a manner than can predict liver fibrosis earlier than other known methods.

Accordingly, disclosed herein are methods and articles for determining the progression or regression of liver fibrosis, or for diagnosing liver disease, in a subject. In some embodiments, the method comprises detecting differential expression of at least twenty-five separate genes listed in Table 4, or the orthologs thereof corresponding to the subject. In some embodiments, the method comprises detecting differential expression of at least twenty-five genes selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof, in a biological sample from the subject. In some embodiments, the methods comprise detecting differential expression of at least 30, at least 35, at least 40, at least 45, or at least 50 genes selected from Table 4. In some embodiments, the methods comprise detecting differential expression of at least 25, at least 30, at least 35, at least 40, at least 45, or at least 50 proteins, peptides and/or amino acids which is encoded by a gene set forth in Table 4, or corresponding mammalian orthologs thereof. In some embodiments, the methods comprise detecting differential expression of at least 25, at least 30, at least 35, at least 40, at least 45, or at least 50 gene regulators which correspond to a gene set forth in Table 4, or corresponding mammalian orthologs thereof. In yet another embodiment the gene regulators can be detected in plasma or serum.

In some embodiments, the methods are useful for detecting early stage liver disease in a subject, such as by assaying a biological sample from a subject for differential expression of at least twenty-five separate genes selected from Table 4 and orthologs thereof, wherein the differential expression of the at least twenty-five genes is indicative of early stage liver disease in the subject. In some embodiments, the methods involve assaying the biological sample from the subject for differential expression of at least 30, at least 35, at least 40, at least 45, or at least 50 genes selected from Table 4. In some embodiments, the at least twenty-five genes are selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof. In some embodiments, the methods comprise detecting differential expression of at least 25, at least 30, at least 35, at least 40, at least 45, or at least 50 proteins, peptides and/or amino acids which is encoded by a gene set forth in Table 4, or corresponding mammalian orthologs thereof. In some embodiments, the methods comprise detecting differential expression of at least 25, at least 30, at least 35, at least 40, at least 45, or at least 50 gene regulators which correspond to a gene set forth in Table 4, or corresponding mammalian orthologs thereof. In yet another embodiment the gene regulators can be detected in plasma or serum. In some embodiments, the different expression is increased expression relative to a control.

In some embodiments, differential expression of each of the at least twenty-five genes in an amount of at least 0.5 fold ($\log_2$) as compared to a control is indicative of early stage liver disease. In some embodiments, differential expression of at least one of the at least twenty-five genes by at least 0.6, 0.7, 0.8, 0.9, 1.0, 1.1, 1.2, 1.3, 1.4 or 1.5, 2.0, 2.5, or 3 fold ($\log_2$) as compared to a control is further indicative of early stage liver disease. In some embodiments, differential expression of each of at least 25 proteins, peptides and/or amino acids by an amount of at least 0.5 fold ($\log_2$) as compared to a control is indicative of early stage liver disease. In some embodiments, differential expression of at least one of the at least 25 proteins, peptides and/or amino acids by an amount of at least 0.6, 0.7, 0.8, 0.9, 1.0, 1.1, 1.2, 1.3, 1.4 or 1.5, 2.0, 2.5, or 3 fold ($\log_2$) as compared to a control is indicative of early stage liver disease. In some embodiments, differential expression of each of at least 25 gene regulators by an amount of at least 0.5 fold ($\log_2$) as compared to a control is indicative of early stage liver disease. In some embodiments, differential expression of at least one of the at least 25 gene regulators by an amount of at least 0.6, 0.7, 0.8, 0.9, 1.0, 1.1, 1.2, 1.3, 1.4 or 1.5, 2.0, 2.5, or 3 fold ($\log_2$) as compared to a control is indicative of early stage liver disease.

In some embodiments, increased expression at least twenty-five genes selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, Fbn1; Col4a1; Sod2; Cyp2c11; Igfbp3; Cxcl12; Angptl3; Igfals; Tgfb1; Vtn; Vhl; and orthologs thereof, is indicative of early stage liver disease.

In some embodiments, increased expression of at least one protein, peptide or amino acid which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ce12; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-DMd; Capg; Pkm2; Ce12; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24, and mammalian orthologs thereof.

In some embodiments, increased expression of least twenty-five genes are selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2, and orthologs thereof, is indicative of early stage liver disease.

In some embodiments, increased expression of at least one protein, peptide or amino acids which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1;

Tagln2; RT1-Da; Capg; Pkm2; Cc/2; Serpine1; Cyba; Fam105a; Cxcl1; Vim; C1qb, Pcolce; Fxyd5; Arpc1b; S100a6; Plau; Itgal; Plod2; Ctgf Col1a2; Igfbp2, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Cc/2; Serpine1; Cyba; Fam105a; Cxcl1; Vim; C1qb, Pcolce; Fxyd5; Arpc1b; S100a6; Plau; Itgal; Plod2; Ctgf Col1a2; Igfbp2, and mammalian orthologs thereof.

In some embodiments, increased expression of at least twenty-five genes selected from the group consisting of: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and n orthologs thereof, is indicative of early stage liver disease.

In some embodiments, increased expression of at least one protein, peptide or amino acids which is encoded by a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and mammalian orthologs thereof.

In some embodiments, increased expression of at least one gene regulator which corresponds to a gene selected from the following group is indicative of early stage liver disease: Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce, and mammalian orthologs thereof.

In some embodiments, decreased expression of a gene selected from the group consisting of: Cyp2c11; Igfbp3; Cxcl12; Angptl3; Igfals; Tgfb1; Vtn; Vhl; and orthologs thereof is indicative of early stage liver disease.

In some embodiments, decreased expression of at least one protein, peptide or amino acid which is encoded by a gene selected from the following group is indicative of early stage liver disease: Cyp2c11; Igfbp3; Cxcl12; Angptl3; Igfals; Tgfb1; Vtn; Vhl; and mammalian orthologs thereof.

In some embodiments, decreased expression of at least one gene regulator which corresponds to a gene selected from the following group is indicative of early stage liver disease: Cyp2c11; Igfbp3; Cxcl12; Angptl3; Igfals; Tgfb1; Vtn; Vhl; and mammalian orthologs thereof.

Expression of any one or more of Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfbp2; Igfbp3; Igfals; Lamac2; Lgals1; Lgals3; Lrp1; Plod2; Pkm; S100a11; S100a6; Serpine1; Serping1; Vim, and orthologs thereof, has not heretofore been associated with liver fibrosis or liver disease. Thus, in some embodiments, there are provided methods of detecting the expression of at least one of these genes, or quantifying levels of mRNA, miRNA or cDNA corresponding to at least one of these genes, in a biological sample from a subject.

In some embodiments, the subject is suspected of having, or at risk of developing, liver disease or liver fibrosis. In some embodiments, differential expression of at least one of these gene compared to a control is determined. In some embodiments, increased expression of at least one of Fam102b; Fam105a; Gpnmb; Pcolce; RT1-Da; RT1-DMA; Slc25a24; Sod2; Tagln2; Arpc1b; Angptl3; Anxa2; Cd53; Cd9; Cp; C1qb; Fxyd5; Igfbp1; Igfbp2; Lamac2; Lgals1; Lgals3; Plod2; Pkm; S100a11; S100a6; Serpine1; Vim; and orthologs thereof is detected and, optionally, indicative of liver disease or liver fibrosis.

In some embodiments, decreased expression of at least one of Angptl3; Igfbp3; Igfals; and orthologs thereof is detected, and, optionally, indicative of liver disease or liver fibrosis. In any of these embodiments, detecting expression of the at least one gene comprises contacting nucleic acid from the biological sample with at least one detectably labelled oligonucleotide specifically hybridizable with the gene, or by other methods described below.

In some embodiments, the methods disclosed herein detect early stage liver disease with a sensitivity of at least 70%, 75%, 80%, 85%, 90%, or at least 95% sensitivity. In some embodiments, the methods disclosed herein detect early stage liver disease with at least 70%, 75%, 80%, 85%, 90%, or at least 95% specificity.

In any of the embodiments described herein, the biological sample may be selected from blood, plasma, serum, urine, or a liver biopsy.

Also disclosed are methods of identifying a compound that increases or decreases the expression of at least one gene associated with hepatotoxicity comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2, Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof; contacting the cell with a test compound; and determining whether the expression of the at least one gene is increased or decreased in the presence of the test compound.

Also disclosed are methods of identifying a compound that increases or decreases the expression of at least one protein, peptide or amino acid which is encoded by a gene associated with hepatotoxicity comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2, Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof; contacting the cell with a test compound; and determining whether the expression of the at least one gene is increased or decreased in the presence of the test compound.

Also disclosed are methods of identifying a compound that increases or decreases the expression of at least one gene regulator which corresponds to a gene associated with hepatotoxicity comprising providing a cell expressing at least one gene selected from Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2, Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof; contacting the cell with a test compound; and determining whether the expression of the at least one gene is increased or decreased in the presence of the test compound.

In some of these embodiments, the at least one gene is selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfbp2; Igfbp3; Igfals; Lamac2; Lgals1; Lgals3; Lrp1; Plod2; Pkm; S100a11; S100a6; Serpine1; Serping1; Vim, and orthologs thereof, and the method comprises determining whether the expression of the at least one gene is decreased in the presence of the test compound.

In some of these embodiments, the at least one gene is selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfbp2; Igfbp3; Igfals; Lamac2; Lgals1; Lgals3; Lrp1; Plod2; Pkm; S100a11; S100a6; Serpine1; Serping1; Vim, and orthologs thereof, and the method comprises determining whether the expression of the at least one protein, peptide or amino acid which is encoded by the gene is decreased in the presence of the test compound.

In some of these embodiments, the at least one gene is selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfbp2; Igfbp3; Igfals; Lamac2; Lgals1; Lgals3; Lrp1; Plod2; Pkm; S100a11; S100a6; Serpine1; Serping1; Vim, and orthologs thereof, and the method comprises determining whether the expression of the at least one gene regulator which corresponds to the gene is decreased in the presence of the test compound.

In some embodiments, the at least one gene is selected from the group consisting of: Cyp2c11; Igfbp3; Cxcl12; Angptl3; Igfals; Tgfb1; Vtn; Vhl; and othologs thereof and the method comprises determining whether the expression of the at least one gene is increased in the presence of the test compound.

In some embodiments, the at least one gene is selected from the group consisting of: Cyp2c11; Igfbp3; Cxcl12; Angptl3; Igfals; Tgfb1; Vtn; Vhl; and othologs thereof and the method comprises determining whether the expression of the at least one protein, peptide or amino acid which is the encoded the gene is increased in the presence of the test compound.

In some embodiments, the at least one gene is selected from the group consisting of: Cyp2c11; Igfbp3; Cxcl12; Angptl3; Igfals; Tgfb1; Vtn; Vhl; and othologs thereof and the method comprises determining whether the expression of the at least one gene regulator which corresponds to the gene is increased in the presence of the test compound.

Also disclosed are methods of treating liver disease, comprising administering to a subject in need thereof, a therapeutically effective amount of a compound identified as decreasing the expression of at least one gene selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfb2; Igfbp3; Igfals; Lamac2; Lgals1; Lgals3; Lrp1; Plod2; Pkm; S100a11; S100a6; Serpine1; Serping1; Vim, and othologs thereof, and/or increasing the expression of at least one gene selected from the group consisting of Cyp2c11; Igfbp3; Cxcl12; Angptl3; Igfals; Tgfb1; Vtn; Vhl; and other orthologs thereof.

Also disclosed are methods of treating liver disease, comprising administering to a subject in need thereof, a therapeutically effective amount of a compound identified as decreasing the expression of at least one protein, peptide or amino acids encoded by a gene selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfb2; Igfbp3; Igfals; Lamac2; Lgals1; Lgals3; Lrp1; Plod2; Pkm; S100a11; S100a6; Serpine1; Serping1; Vim, and othologs thereof, and/or increasing the expression of at least one protein, peptide or amino acids which corresponds to a gene selected from the group consisting of Cyp2c11; Igfbp3; Cxcl12; Angptl3; Igfals; Tgfb1; Vtn; Vhl; and other orthologs thereof.

Also disclosed are methods of treating liver disease, comprising administering to a subject in need thereof, a therapeutically effective amount of a compound identified as decreasing the expression of at least one gene regulator which corresponds to a gene selected from the group consisting of: Dsc2; Fam102b; Fam105a; Gpnmb; Pcolce; RT1-Da; RT1-DMA; Slc25a24; Tagln2; Arpc1b; Angptl3; Anxa2; Cd53; Cd9; Cp; C1qb; Fxyd5; Igfb2; Igfbp3; Igfals; Lamac2; Lgals1; Lgals3; Lrp1; Plod2; Pkm; S100a11; S100a6; Serpine1; Serping1; Vim, and othologs thereof, and/or increasing the expression of at least one gene regulator which corresponds to a gene selected from the group consisting of Cyp2c11; Igfbp3; Cxcl12; Angptl3; Igfals; Tgfb1; Vtn; Vhl; and other orthologs thereof.

In any of the embodiments described herein, differential expression may be determined by quantification of the levels of the proteins encoded by the genes. In some embodiments, wherein quantification of the levels of the proteins comprises assaying a sample by Western blotting, ELISA or mass spectrometry.

In any of the embodiments described herein, differential expression may be determined by quantification of the levels of mRNA corresponding to the at least twenty-five genes. In some embodiments, quantification of the levels of the mRNA comprises incubating the mRNA, miRNA, or corresponding cDNA thereof, with an oligonucleotide array. In some embodiments, the mRNA, miRNA or corresponding cDNA thereof, is hybridized to the oligonucleotide array by interaction with a capture probe, wherein the hybridization results in a target:capture probe pair. In some embodiments, the target:capture probe pair is labeled with a biotinylated label probe. In some embodiments, streptavidin-conjugated phycoerythrin (SAPE) is bound to the biotinylated label probe.

Further disclosed herein is an array comprising at least twenty-five target oligonucleotides immobilized on a substrate, wherein each target oligonucleotide comprises a sequence that is specifically hybridizable to mRNA, cDNA or miRNA corresponding to one of at least twenty-five separate genes from Table 4, or orthologs thereof, such that the array comprises at least one target oligonucleotide specifically hybridizable to each of at least twenty-five different genes, such as at least twenty-five selected from Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; or orthologs thereof. In some embodiments, the target oligonucleotides are labelled with a detectable label. In some embodiments, the target oligonucleotides comprise cDNA specific sequence, wherein said cDNA specific sequence comprises at least one nucleotide difference from corresponding genomic DNA. In some embodiments, the target oligonucleotides are labelled directly with a detectable label. In some embodiments, the target oligonucleotides are labelled indirectly with a detectable label. In some embodiments, the detectable label comprises biotin. In some embodiments, streptavidin-conjugated phycoerythrin (SAPE) is bound to the biotin. In some embodiments, the target oligonucleotide is immobilized on the substrate due to binding with a capture probe. In some embodiments, the capture probe is directly immobilized on the surface of the substrate. In some embodiments, the capture probe is indirectly immobilized on the surface of the substrate. In some embodiments, the array further comprises a label extender.

Also disclosed are handheld apparatuses comprising an array as disclosed herein.

Also disclosed are kits for the diagnosis of liver disease, comprising at least twenty-five detectably labelled oligonucleotides, wherein each oligonucleotides comprises a sequence that is specifically hybridizable to mRNA, cDNA or miRNA corresponding to one of at least twenty-five separate genes from Table 4, or orthologs thereof, such that the kit comprises at least one detectably labelled oligonucleotide specifically hybridizable to mRNA, cDNA or miRNA corresponding to each of the at least twenty-five genes, such as at least twenty-five selected from Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof.

Also disclosed are kits for the diagnosis of liver disease, comprising at least twenty-five antibodies, or antigen-binding fragments thereof, wherein each antibody or fragment thereof is capable of specifically binding to one of at least twenty-five separate proteins encoded by genes from Table 4, or orthologs thereof, such that the kit comprises at least one antibody or antigen-binding fragment thereof that specifically binds to each of the at least twenty-five separate proteins, such as at least twenty-five selected from proteins encoded by Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Cyba; Fam105a; Cxcl1; Vim; C1qb; Pcolce; Fxyd5; Arpc1b; S100a6; Plau; Itgal; Plod2; Ctgf; Col1a2; Igfbp2; Lox; Fam102b; CD53; Itgb2; Lamc2; Cp; Slc25a24; Fbn1; Col4a1; Sod2; Cyp2c11; Igfbp3; Cxcl12; Angptl3; Igfals; Tgfb1; Vtn; Vhl; and orthologs thereof.

Also disclosed are kits for the diagnosis of liver disease, wherein at least twenty-five separate proteins encoded by genes from Table 4, or orthologs thereof, are directly identified from the spectra of a high accuracy instrument.

EXAMPLES

Example 1—Differential Expression Analysis—mRNA mRNA is isolated and purified from lysed tissue biopsy specimens. The target mRNA is incubated with beads conjugated to capture probes (each probe is an oligonucleotides specific for one of the genes in the panel). The target is hybridized to the probe by a capture extender-capture probe interaction. Specific mRNA targets hybridize overnight to the respective beads. The signal is amplified by incubating mRNA-capture probe pairs by affixing an amplifier affixed to a biotinylated label probe. Streptavidin-conjugated phycoerythrin (SAPE) is bound to the biotinylated probe to amplify the signal. The signal is detected and quantified by Bioplex suspension array instrumentation, which measures the SAPE fluorescence signal proportional to the amount of mRNA transcripts captured by the bead.

Example 2—Differential Expression Analysis—Proteins

Blood and urine specimens are interrogated by standard sandwich enzyme-linked immunosorbent assays (ELISAs) to detect circulating and/or urinary levels of proteins. Briefly, a capture antibody specific for the target analyte is conjugated to the lower surface of a 96-well plate. Plasma, urine, or serum specimens are incubated with the capture antibody to bind analytes in the biofluid. Non-specific proteins are washed away, and the signal is amplified by incubating with a biotinylated secondary antibody, followed by a streptavidin-conjugated amplifier. After washing away non-specific analytes, a colorimetric reagent is added, causing a color change directly proportional in intensity to the amount of target analyte in the sample. A spectrophotometer is used to quantify the change absorbance, and the exact quantity is measured by comparing the absorbance to a standard curve of known concentrations of the target analyte.

Example 3—Determination of Gene Panel

A gene panel was determined using two computational approaches: (1) a co-expression modules approach using iterative signature algorithms (ISA) (Tawa G J, Abdul-Hameed M D, Yu X, et al. Characterization of chemically induced liver injuries using gene co-expression modules. PLoS One 2014; 9(9):e107230) and (2) a pathway and network analysis approach (AbdulHameed M D, Tawa G J, Kumar K, et al. Systems level analysis and identification of pathways and networks associated with liver fibrosis. PLoS One 2014; 9(11):e112193). DrugMatrix liver gene expression data generated using Affymetrix GeneChip Rat Genome 230 2.0 Arrays was used for further analysis. In the co-expression modules approach, genes were grouped into 78 distinct co-expression modules based on similarity of expression patterns across conditions, each condition defined as a particular compound-dose combination. The characteristic of correlated expression inherent in these modules implied that the module genes are associated with a common biochemical process. The resultant gene co-expression modules can be members of multiple modules. This is consistent with the fact that genes are, in general, associated with multiple biochemical pathways. Gene co-expression modules associated with liver fibrosis were identified as those exhibiting an average absolute activation value >1.5 times control when exposed to compound-dose combinations that cause fibrosis 4. Center genes were identified from these modules as those with absolute activation closest to the module average. These center genes were chosen to be part of a multiplex panel.

In the pathway and network analysis approach, liver fibrosis-relevant genes were identified and mapped to pathways and high-confidence human protein-protein interaction (PPI) networks. The standard differential expression and co-expression analysis approach was carried out using rank product and hierarchical clustering, respectively, to identify liver fibrosis-relevant genes (see, e.g., Gentleman R C, Carey VJ, Bates D M, et al. Bioconductor: open software development for computational biology and bioinformatics. Genome biology 2004; 5(10):R80; and Breitling R, Armengaud P, Amtmann A, Herzyk P. Rank products: a simple, yet powerful, new method to detect differentially regulated genes in replicated microarray experiments. FEBS letters 2004; 573(1-3):83-92). These genes were mapped to high-confidence human PPI networks (Yu X, Wallqvist A, Reifman J (2012) Inferring high-confidence human protein-protein interactions. BMC Bioinformatics 13: 79). Cytoscape tools such as KeyPathway Miner and Clusterviz were used to extract network modules (Alcaraz N, Friedrich T, Kotzing T, et al. Efficient key pathway mining: combining networks and OMICS data. Integrative biology: quantitative biosciences from nano to macro 2012; 4(7):756-764). Network modules represent closely connected regions of the network and are expected to participate in similar function. A network module with high activation score in drug matrix liver fibrosis conditions was extracted and also enriched with known fibrosis-related genes. Differentially expressed genes in this module were chosen to be part of a multiplex panel.

Example 4—Analysis of Differential Expression

Candidate genes identified by co-expression modules and pathway/network approaches were fabricated into a custom gene panel using a commercial source (the QuantiGene 2.0 Plex assay, Affymetrix, Santa Clara, Calif.). A total of 71 genes plus 3 housekeeping genes were selected. Using 150 ng RNA input, samples were processed following manufacturer's instructions for purified RNA with use of the Hand-Held Magnetic Plate Washer. Plates were read immediately following the final wash using the BioPlex 200 instrument (BioRad, Hercules, Calif.). The following parameters were set on the BioPlex instrument: sample size=100 µL; DD Gate=5,000-25,000; Timeout=45 sec; Bead Event/Bead Region=100.

For each sample, the average signal intensity was determined as recommended by the manufacturer. Duplicates were averaged. The average background signal for each gene was subtracted. Assay limit of detection was determined by adding three standard deviations of assay background signals to the average intensity of the background control wells. All intensities lower than the limit of detection for each probe was set to one unit above the probe's limit of detection. Probes with all intensities below the assay limit of detection were removed from the final analysis. The test gene signal was divided by the average intensities of the three normalization genes (Gapdh, Hprt1, Ppib). For each test gene, the fold change was calculated by dividing the normalized value for the treated samples by the normalized value of the vehicle-treated controls. Fold changes were plotted as $\log_2$ fold change. Gene expression data were imported into Partek Genomics Suite 6.0 (Partek, Inc., St. Louis, Mo.). Principal component analysis was used for multivariate interpretation to determine sources of variation across sample groups (Joliffe I T, Morgan B J. Principal component analysis and exploratory factor analysis. Statistical methods in medical research 1992; 1(1):69-95). Differentially expressed genes were determined by analysis of variance (ANOVA) with contrasts, setting the ANOVA factors as toxicant and the histopathological endpoint of fibrosis (any score >0). ANOVA variables were fibrosis score 0 (none) vs. score of >0 (minimal, mild, moderate, and marked). For hierarchical biclustering, differentially expressed genes were standardized by setting the genes expressed to a mean of zero and scaling to a standard deviation of one. Euclidean geometry was used to cluster row and column dissimilarity using a method of average linkage.

Receiver operator curves were generated to determine the sensitivity and specificity of the gene expression assay compared to standard histological approaches.

Example 5—Testing of Gene Panel Fidelity

To demonstrate the fidelity of the gene panels in comparison to the current gold standards in clinical diagnosis (i.e., histopathology from a tissue section or biopsy specimen), a 5-chemical oral exposure study was conducted in rodents and directly compared both methods were directly compared. The following test chemicals were purchased from Sigma Aldrich Corporation (St. Louis, Mo.): 4,4'-methylenedianiline (CAS No. 101-77-9), dexamethasone (CAS No. 50-02-2), allyl alcohol (CAS No. 107-18-6), bromobenzene (CAS No. 108-86-1), and carbon tetrachloride (CAS No. 56-23-5). All chemical compounds were diluted in corn oil (CAS No. 8001-30-7) (MP Biomedicals, LLC (Solon, Ohio)). The dose volume was 5 mL/kg. Doses were selected based on doses published in the DrugMatrix database, the National Toxicology Program reports, and ATSDR reports.

In vivo rat experiments were performed at Integrated Laboratory Systems (ILS, Research Triangle Park, NC). ILS's Institutional Animal Care and Use Committee approved all experimental procedures. Research was conducted in compliance with the Animal Welfare Act, and other Federal statutes and regulations relating to animals and experiments involving animals and adheres to principles stated in the "Guide for Care and Use of Laboratory Animals" as prepared by the Committee on Care and Use of Laboratory Animals of the Institute of Laboratory Animal Resources, National Research Council in facilities that are fully accredited by the Association for Assessment and Accreditation of Laboratory Animal Care, International. Male Sprague-Dawley rats (CD IGS [CRL:CD (SD)]) were purchased from Charles River Laboratories (Stone Ridge, N.Y.). Rats weighing 215-245 g (8 weeks old) were used. Briefly, rats were housed two per cage with a rat tunnel enrichment device (Bio-Serve, Frenchtown, N.J.). Rats were fed a Purina Rodent Diet No. 5002 (Ralston Purina Co., St. Louis, Mo.), supplied ad libitum. Animals received reverse osmosis-treated tap water (City of Durham, N.C.) ad libitum, which was changed at least once weekly. Controls in the animal rooms were set to maintain temperatures between 20-In vivo rat experiments were performed at Integrated Laboratory Systems (ILS, Research Triangle Park, NC). ILS's Institutional Animal Care and Use Committee approved all experimental procedures. Research was conducted in compliance with the Animal Welfare Act, and other Federal statutes and regulations relating to animals and experiments involving animals and adheres to principles stated in the "Guide for Care and Use of Laboratory Animals" as prepared by the Committee on Care and Use of Laboratory Animals of the Institute of Laboratory Animal Resources, National Research Council in facilities that are fully accredited by the Association for Assessment and Accreditation of Laboratory Animal Care, International. Male Sprague-Dawley rats (CD IGS [CRL:CD (SD)]) were purchased from Charles River Laboratories (Stone Ridge, N.Y.). Rats weighing 215-245 g (8 weeks old) were used. Briefly, rats were housed two per cage with a rat tunnel enrichment device (Bio-Serve, Frenchtown, N.J.). Rats were fed a Purina Rodent Diet No. 5002 (Ralston Purina Co., St. Louis, Mo.), supplied ad libitum. Animals received reverse osmosis-treated tap water (City of Durham, N.C.) ad libitum, which was changed at least once weekly. Controls in the animal rooms were set to maintain temperatures between 20-25° C. with a relative humidity of 30-70% and a 12-hour light/12-hour dark cycle, lights on at 6:00 AM. Clinically healthy animals were assigned to dose groups using a procedure that stratifies animals across groups by body weight such that mean body weight of each group was not statistically different from any other group using analysis of variance (Statistical Analysis System version 9.2, SAS Institute, Cary, N.C.). Animals were dosed by oral gavage for five consecutive days (+10 minutes from the previous day's dose administration time). Volume was based upon daily body weight.

Animals were observed cageside one hour following daily dose administration, then 1-2 times per day during dosing regimens. Body weights were measured daily prior to dose administration, and prior to euthanasia. Twenty-four hours after the final dose administration, animals were anesthetized with isoflurane then euthanized by exsanguination followed by decapitation. Livers were harvested at necropsy and weighed to within 0.1 g. One half of the left lobe of the liver was fixed in 10% formalin. The remaining half of the left lobe of the liver was flash frozen in liquid nitrogen, then stored below −70° C. Liver specimens were frozen in less than three minutes from time of death.

Formalin-fixed liver specimens were embedded in paraffin blocks. A 5 μm section of liver from each animal was stained with hematoxylin and eosin, Oil Red 0, or Masson's trichrome for microscopic evaluation. The tissues were evaluated by a Board-Certified veterinarian-pathologist (MHB). Tissues were qualitatively scored for degree of pathology on a descriptive scale with the following distribution: None, 0% of tissue affected; Minimal, >0-30% of tissue affected; Mild, >30-60% of the tissue affected; Moderate, 60-80% of the tissue affected; Marked, >80% of the tissue affected.

Working on dry ice, a portion (−10 mg) of flash-frozen liver was cut from each sample and transferred to a clean, labeled tube. Total RNA was then isolated using Qiagen's miRNeasy 96 kit (Qiagen, Valencia, Calif.) following manufacturer's instructions with a final elution volume of −150 μL (2×75 μL). The quality and quantity of RNA samples were evaluated with a 2100 Bioanalyzer (Agilent Technologies, Santa Clara, Calif.), using the Agilent RNA 6000 Nano Reagents and a multiwell NanoDrop 8000 spectrophotometer (Thermo Fisher Scientific, Waltham, Mass.).

Using 1 μg RNA input, cDNA was generated using a QuantiTect Reverse Transcription kit (Qiagen, Valencia, Calif.) following manufacturer's instructions. Applied Biosystems SYBR Green Master Mix was used in a 20 μL qPCR reaction with 2 μL of cDNA template and a 2.tM final concentration of each primer. A total of five genes were targeted (Gapdh, Actb, Timp1, Tgfb1, and Psma5), two of which served as the endogenous controls (Gapdh and Actb). An Applied Biosystems 7500 Real-Time PCR System (Applied Biosystems, Foster City, Calif.) was used for thermal cycling and fluorescence detection using the default settings for Quantitation-Comparative CT with SYBR® . . . Green Reagents which uses the following scheme: 95° C. for 10 minutes followed by 40 cycles of: 95° C. for 15 seconds, 60° C. for 1 minute, and a fluorescence signal read. Al! primers were obtained from Integrated DNA Technology's PrimeTime qPCR primer library (Integrated DNA Technologies, Coralville, Iowa).

Data was imported into GraphPad Prism (GraphPad Software, Inc.; LaJolla, Calif.) for analysis. A nonparametric Kruskal-Wallis analysis of variance by ranks with post hoc Dunnett's multiple comparison test was used to determine statistical difference among dose groups. A one sample t-test compared to a theoretical mean of 1.0 fold change was used to determine difference from control for each dose group. A p-value<0.05 was used as a cutoff for statistical significance.

Histopathology

Male Sprague-Dawley rats were administered toxicants by oral gavage for five days (see Table 1). At high doses, the fibrogenic chemicals 4,4'-methylenedianiline (FIGS. 1A and 1B) and allyl alcohol (FIGS. 2A and 2B) caused bile duct hyperplasia comorbid with fibrosis and necrosis. Both chemicals caused a dose-dependent increase in the degree of fibrosis, although the fibrosis phenotype showed more heterogeneity among the animals dosed with allyl alcohol than 4,4-methylenedianiline (FIGS. 1C and 2C). Animals receiving the highest doses gained less weight over the five-day exposure interval than their low-dose counterparts (FIGS. 1D and 2D). Gene expression of the fibrosis-related genes Tgfb1 and Timp1 showed a dose-dependent increase as measured by qPCR (FIGS. 1E, 1F, 2E, and 2F).

TABLE 1

Chemical compound-dose groups and presumptive mechanisms of toxicity after oral exposure in rats

| Chemical | Structure | Dose (mg/kg) (n = 4 rats/dose gorup) | Mechanism of Hepatotoxicity | Predicted Histopathology |
|---|---|---|---|---|
| Allyl Alcohol | HO-CH=CH₂ (acrolein: H₂C=CH-CHO) | 0, 4.5, 9.7, 20.9, 45 | Free radical damage by toxic metabolite (acrolein): | Fibrosis, bile duct hyperplasia |
| Bromobenzene | Br-C₆H₅ | 0, 3.1, 19.8, 124.6, 785 | Free radical damage by toxic metabolite: | Fatty liver, necrosis |
| Carbon tetrachloride | CCl₄ | 0, 200, 360.9, 651.2 | Free radical damage by toxic metabolite, lipid peroxidation •CCl₃ | Fatty liver, necrosis, fibrosis (delayed-onset) |

TABLE 1-continued

Chemical compound-dose groups and presumptive mechanisms of toxicity after oral exposure in rats

| Chemical | Structure | Dose (mg/kg) (n = 4 rats/dose group) | Mechanism of Hepatotoxicity | Predicted Histopathology |
|---|---|---|---|---|
| Dexamethasone | 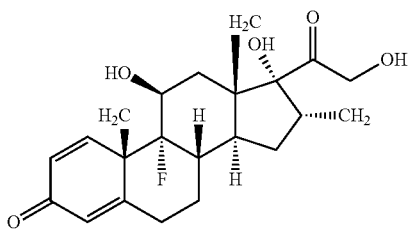 | 0, 1, 6.7, 44.8, 300 | Indirect lipid accumulation by increased circulating triglycerides | Minimal; glycogen accumulation |
| 4,4'-Methylenedianiline (MDA) | 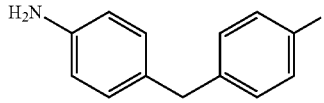 | 0, 8.1, 22, 59.7, 162 | Conversion to toxic metabolite by n-acetyl-transferase enzymes | Fibrosis, necrosis, bile duct hyperplasia |

Carbon tetrachloride caused a dose-dependent increase in vacuolation indicative of lipid accumulation without evidence of fibrosis (FIGS. 3A-3D). Body weight gain was less than controls at all doses (FIG. 3E). The fibrosis-dependent gene Tgfb1 was not significantly upregulated at any dose (FIG. 3F).

All doses of dexamethasone resulted in lipemia (milky white plasma) and marked cytoplasmic alteration characteristic of glycogen accumulation (FIGS. 4A-4C), although a definitive confirmation could not be made without periodic acid Schiff s stain. The highest dose caused moderate tissue necrosis affecting >60-80% of the tissue in two animals, resulting in a concomitant decrease in percentage of tissue which could be scored for cytoplasmic alteration (FIG. 4C, 300 mg/kg dose). Body weight loss occurred at all doses (FIG. 4D). Tgfb1 was significantly downregulated in animals receiving 1, 6.7, or 300 mg/kg dexamethasone (FIG. 4E). Dexamethasone administration at 44.8 mg/kg caused a similar trend, but the difference was not statistically significant (FIG. 4E). Timp1 expression was more variable among individual animals, but none of the changes were statistically significant (FIG. 4F).

The non-fibrogenic toxicant bromobenzene did not cause histopathological evidence of bile duct hyperplasia or fibrosis at any dose (FIGS. 5A and 5B), but the highest dose caused varying degrees of vacuolation in all experimental animals (FIG. 5C). The observed pathology is consistent with bromobenzene's toxicological classification as a potent inducer of hepatic steatosis. The highest dose of bromobenzene resulted in body weight loss over the study interval (FIG. 5D). Tgfb1 and Timp1 expression were not significantly affected at any dose (FIGS. 5E and 5F; $p>0.05$). However, expression of Psma5, a gene associated with periportal lipid accumulation, was increased in the high-dose group with observable vacuolation pathology ($2.2\pm0.8$-fold vehicle control; $p<0.05$).

Figure 6D:
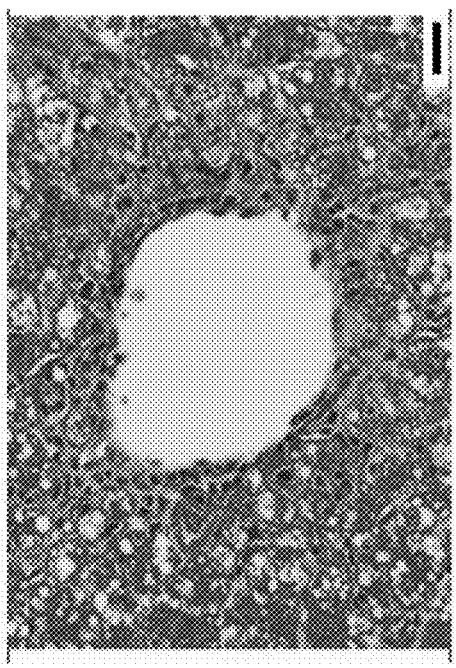
Figure 6A:
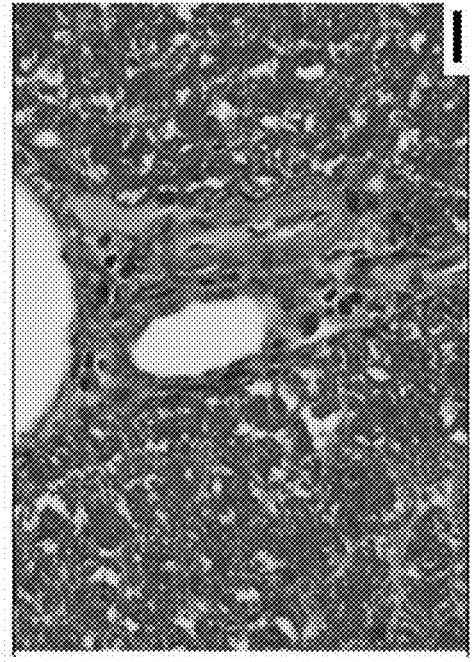
Figure 6C:
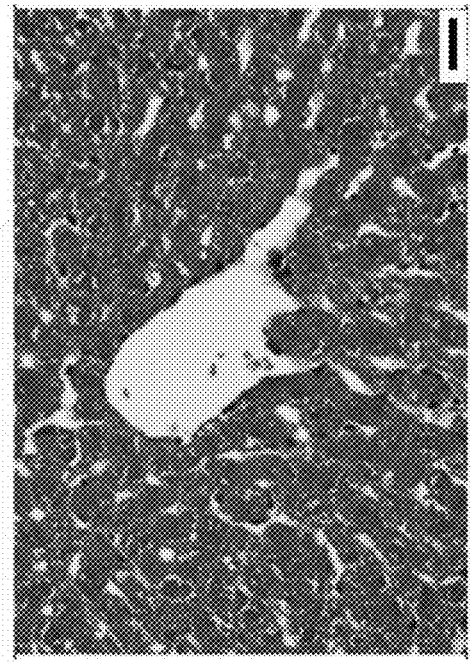

Perioportal fibrosis was confirmed by Masson's trichrome staining after 4,4'-methylenediani line administration (162 mg/kg/day) (FIGS. 6A and 6B). Carbon tetrachloride (200 mg/kg/day) caused prefibrotic centrilobular collagenous accumulation (FIGS. 6C and 6D).

Multiplexed Fibrosis Gene Panel

Chemical-dose groups were down-selected based on histopathology to conform to the 96-well assay format of the multiplexed panel of presumptive fibrosis genes. Three of the four dose groups were evaluated for the fibrogenic chemicals allyl alcohol and 4,4'-methylenedianiline. A single dose was selected with group-matched vehicle controls for each of the remaining chemicals. The lowest doses of both carbon tetrachloride and dexamethasone were selected because all doses produced comparable histopathology in both cases. The highest dose of bromobenzene was selected because the vacuolation pathology was only observed at this dose.

Isolated liver RNA was incubated with microbead-bound capture probes specific for the 71 presumptive fibrogenic genes and three housekeeping normalization genes. All fluorescence intensity values for four genes (Dram1, Myoc, Pdgf, and Lama5) fell below the limits of assay detection. These genes were excluded from further analysis. For a complete list of differentially expressed genes, please refer to Table 2.

TABLE 2

| Differential Expression of Genes in Rats After Exposure to Toxicants | | | | | | |
|---|---|---|---|---|---|---|
| Animal Number | 89 | 90 | 91 | 92 | 9 | 10 |
| Toxicant | 4,4'-MDA | 4,4'-MDA | 4,4'-MDA | 4,4'-MDA | Allyl Alcohol | Allyl Alcohol |
| Dose (mg/kg) | 22 | 22 | 22 | 22 | 9.7 | 9.7 |
| Inflammation | 0 | 0 | 0 | 0 | 0 | 0 |
| Vacuolation | 0 | 0 | 0 | 0 | 0 | 0 |
| Bile Duct Hyperplasia and Fibroplasia | 0 | 0 | 0 | 0 | 0 | 0 |
| Cytoplasmic Alteration | 2 | 1 | 3 | 1 | 1 | 1 |
| Necrosis | 0 | 0 | 0 | 0 | 0 | 0 |

TABLE 2-continued

Differential Expression of Genes in Rats After Exposure to Toxicants

| Gapdh | 2112 | 2068 | 1825.5 | 1732.5 | 1566.3 | 1899 |
|---|---|---|---|---|---|---|
| Hprt1 | 577.5 | 739.8 | 496.5 | 405.5 | 431.3 | 482.5 |
| Ppib | 1429.5 | 1416.3 | 1158 | 1094.3 | 1091.5 | 1442.5 |
| A2m | −2.855 | −0.021 | −2.439 | −1.215 | −0.770 | 0.285 |
| Cxcl1 | −0.229 | −0.253 | 0.128 | 0.197 | 0.698 | 1.963 |
| RT1-DMa | −0.243 | −0.620 | −0.341 | 0.126 | −0.785 | −0.228 |
| Arf6 | −0.068 | −0.041 | −0.364 | 0.202 | −0.534 | −0.308 |
| Dsc2 | 0.089 | −0.493 | −0.175 | 0.540 | −0.340 | −0.708 |
| Sod2 | −0.025 | −0.010 | −0.185 | 0.179 | −0.155 | −0.147 |
| Cxcl16 | −0.760 | −2.494 | −1.507 | 0.503 | −4.079 | −0.608 |
| Lame2 | −0.986 | −1.330 | −1.051 | 1.090 | −4.514 | −0.668 |
| Ccl2 | −0.478 | −2.306 | −1.102 | 0.769 | −4.934 | −1.072 |
| Col5a2 | −0.430 | −2.096 | −0.679 | 0.566 | −6.430 | −0.644 |
| Arrb1 | −0.607 | −1.924 | −1.789 | 0.833 | −5.190 | −0.975 |
| Vhl | −0.894 | −1.708 | −1.342 | 0.643 | −5.780 | −0.518 |
| Ctgf | −0.987 | −1.256 | −2.405 | 0.339 | −1.559 | −0.144 |
| Lcn2 | −0.695 | −0.526 | −0.938 | −0.318 | −4.722 | −0.302 |
| Lbp | −0.004 | −0.228 | −0.249 | 0.126 | 0.122 | 0.174 |
| S100A11 | 0.125 | −0.544 | −0.369 | 0.746 | −1.913 | −0.593 |
| Pkm2 | 0.151 | −0.187 | −0.404 | 0.171 | −0.384 | −0.109 |
| Tagln2 | 0.349 | −0.487 | −0.149 | 0.259 | −0.358 | −0.197 |
| Cyba | 0.311 | −0.537 | −0.253 | 0.192 | −0.552 | −0.259 |
| Capg | −0.223 | −0.640 | −0.784 | 0.094 | −0.909 | −0.679 |
| C1qb | 0.133 | −0.701 | −0.250 | 0.301 | 0.144 | −0.221 |
| Plau | −0.214 | −0.629 | −0.813 | 0.201 | −1.777 | −1.011 |
| Fstl1 | 0.242 | −0.419 | 0.004 | 0.448 | −0.414 | −0.240 |
| Vim | 0.268 | −0.815 | −0.412 | 0.554 | 0.068 | −0.253 |
| Col4a1 | −0.158 | −0.477 | −0.335 | 0.500 | −0.348 | −0.006 |
| Fbn1 | −0.228 | −0.665 | −0.692 | 0.339 | −0.675 | −0.004 |
| Nid1 | 0.048 | −0.571 | −0.071 | 0.340 | −0.885 | −0.486 |
| Col1a1 | −0.465 | −2.285 | −1.409 | 0.321 | −0.671 | −0.901 |
| Lgals1 | 0.667 | −1.034 | −0.065 | 0.713 | −1.446 | −1.536 |
| Arpc1b | −0.510 | −1.326 | −1.129 | 0.324 | −4.326 | −0.855 |
| CD53 | −0.379 | −1.429 | −1.351 | −0.278 | −0.554 | −0.680 |
| Itgb2 | −0.044 | −0.559 | −0.772 | 0.441 | −1.022 | −0.073 |
| Itga1 | −0.084 | −0.862 | −0.531 | −0.224 | −0.128 | −0.334 |
| RT1-Da | 0.436 | −0.623 | −0.441 | −0.237 | −0.530 | −0.349 |
| Lgals3bp | −0.334 | −1.112 | −0.592 | 0.101 | −1.460 | −0.288 |
| Pcolce | −0.165 | −0.858 | −0.115 | 0.247 | −1.394 | −0.468 |
| CP | 0.011 | 0.004 | −0.198 | 0.329 | 0.011 | 0.156 |
| Igfbp2 | −0.276 | −0.608 | −1.094 | 0.428 | −4.542 | 0.141 |
| CD9 | −0.052 | −0.660 | −0.131 | 0.455 | −2.005 | 0.118 |
| Serpine1 | −0.318 | −0.576 | −0.297 | 0.540 | −3.045 | −0.265 |
| Lox | −0.021 | 0.268 | −0.131 | 0.718 | −3.732 | −0.312 |
| Plod2 | −0.334 | −0.460 | −0.434 | 0.789 | −3.558 | −0.059 |
| Plat | 0.246 | −0.329 | −0.433 | 0.878 | −3.393 | −0.378 |
| Slc25a24 | −0.090 | −0.239 | 0.153 | 0.682 | −3.758 | −0.208 |
| Fam102b | −0.168 | −0.683 | −0.353 | 0.253 | −3.759 | −0.607 |
| Col1a2 | −0.675 | −1.296 | −0.898 | 0.391 | −4.077 | −0.239 |
| Fxyd5 | −0.040 | −0.415 | −0.228 | 0.500 | −2.713 | 0.100 |
| Fam105a | −0.331 | −0.801 | −0.384 | 0.473 | −2.213 | −0.816 |
| Timp1 | 0.232 | −0.937 | −0.283 | 0.424 | −4.028 | −1.429 |
| S100A6 | −0.139 | −0.974 | −0.468 | 0.537 | −1.038 | −0.283 |
| Lgals3 | 0.120 | −0.871 | −0.263 | 0.423 | −0.193 | −0.673 |
| Gpnmb | −0.185 | −1.170 | −1.038 | −0.108 | −1.018 | −0.944 |
| Anxa2 | 0.641 | −0.897 | −0.674 | 0.911 | −2.047 | −0.783 |
| Lum | −1.405 | −0.867 | −1.587 | 0.340 | −0.529 | −1.211 |
| Mmp2 | −0.393 | −0.668 | −0.568 | 0.049 | −0.238 | −0.147 |
| Igfbp1 | −1.313 | −0.371 | −0.485 | 1.098 | −0.901 | 0.209 |
| Cyp2c11 | −0.399 | −0.060 | 0.353 | −0.018 | 0.297 | 0.524 |
| Angptl3 | −0.284 | −0.570 | −0.082 | 0.202 | −0.018 | 0.212 |
| Apoc | −0.107 | −0.053 | −0.016 | 0.120 | 0.502 | 0.059 |
| Vtn | −0.090 | −0.056 | 0.010 | 0.229 | 0.290 | 0.216 |
| Tgfb1 | −0.117 | −0.343 | −0.283 | 0.105 | −0.040 | 0.073 |
| Igfbp3 | −0.436 | −0.102 | −0.746 | 0.167 | −0.267 | −0.489 |
| Cxcl12 | −0.092 | −0.288 | 0.201 | 0.478 | −0.268 | −0.666 |
| Igfals | −0.182 | −0.197 | −0.087 | 0.156 | 0.094 | −0.511 |
| Serping1 | −0.336 | −0.214 | 0.339 | 0.319 | −0.200 | −0.502 |
| Fn1 | −0.437 | −0.481 | −0.339 | 0.548 | −0.074 | −0.267 |
| Lrp1 | −0.604 | −0.180 | −0.192 | 0.366 | −0.150 | 0.136 |
| Animal Number | 11 | 12 | 13 | 14 | 15 | 16 |
| Toxicant | Allyl Alcohol | Allyl Alcohol | Allyl Alcohol | Allyl Alcohol | Allyl Alcohol | Allyl Alcohol |
| Dose (mg/kg) | 9.7 | 9.7 | 20.9 | 20.9 | 20.9 | 20.9 |
| Inflammation | 0 | 0 | 0 | 0 | 2 | 3 |
| Vacuolation | 0 | 0 | 0 | 0 | 0 | 0 |

TABLE 2-continued

Differential Expression of Genes in Rats After Exposure to Toxicants

| | | | | | | |
|---|---|---|---|---|---|---|
| Bile Duct Hyperplasia and Fibroplasia | 0 | 0 | 0 | 0 | 2 | 3 |
| Cytoplasmic Alteration | 1 | 1 | 1 | 2 | 3 | 2 |
| Necrosis | 0 | 0 | 0 | 0 | 2 | 3 |
| Gapdh | 2050.3 | 1558 | 1911.5 | 2293 | 2276 | 1773.8 |
| Hprt1 | 455 | 501.3 | 593.8 | 565 | 581 | 463.5 |
| Ppib | 1395.5 | 1320.5 | 1609 | 1773.5 | 1742.5 | 1158 |
| A2m | −0.080 | −0.772 | 0.452 | −0.406 | 2.458 | 0.711 |
| Cxcl1 | 0.048 | 0.812 | 0.826 | 0.452 | 3.867 | 0.282 |
| RT1-DMa | −0.025 | 0.294 | 0.011 | −0.537 | 1.420 | 0.385 |
| Arf6 | −0.150 | −0.051 | −0.119 | −0.124 | −0.060 | 0.108 |
| Dsc2 | −0.364 | −0.085 | 0.025 | 0.042 | 0.670 | −0.244 |
| Sod2 | −0.049 | −0.003 | −0.150 | −0.185 | 0.200 | −0.023 |
| Cxcl16 | −0.040 | −2.546 | −0.063 | −0.389 | 0.608 | 0.071 |
| Lame2 | −0.178 | −1.023 | −0.146 | 0.242 | 0.365 | 0.350 |
| Ccl2 | 0.278 | −1.816 | 0.305 | 0.076 | 0.418 | −0.004 |
| Col5a2 | −0.269 | −0.739 | −0.019 | −0.137 | 0.062 | −0.045 |
| Arrb1 | −0.536 | −0.907 | 0.124 | −0.102 | 0.150 | −0.304 |
| Vhl | −0.121 | −1.756 | 0.190 | 0.135 | 0.177 | −0.003 |
| Ctgf | −0.814 | −3.246 | −0.229 | −0.151 | 0.546 | 0.297 |
| Lcn2 | 0.299 | −0.168 | −1.307 | 1.010 | 5.978 | −1.214 |
| Lbp | 0.547 | 0.615 | 0.532 | −0.106 | 2.498 | 1.177 |
| S100A11 | −0.053 | −0.021 | −0.359 | −0.460 | 0.260 | −0.150 |
| Pkm2 | −0.206 | 0.242 | 0.058 | −0.245 | 0.861 | −0.360 |
| TagIn2 | −0.024 | −0.050 | 0.310 | −0.106 | 0.495 | −0.144 |
| Cyba | −0.173 | 0.122 | 0.022 | −0.226 | 1.469 | −0.265 |
| Capg | −0.556 | −0.212 | −0.107 | −0.055 | 1.543 | −0.192 |
| C1qb | 0.063 | 0.323 | 0.247 | −0.106 | 1.217 | 0.232 |
| Plau | −0.288 | 0.087 | 0.010 | −0.305 | 1.013 | 0.357 |
| Fstl1 | −0.177 | 0.328 | 0.041 | −0.134 | −0.516 | −0.127 |
| Vim | 0.161 | 0.556 | 0.029 | −0.100 | 1.145 | −0.108 |
| Col4a1 | −0.296 | 0.343 | −0.444 | 0.012 | −0.344 | 0.685 |
| Fbn1 | −0.371 | 0.561 | −0.379 | −0.744 | −0.664 | −0.101 |
| Nid1 | −0.174 | −0.195 | 0.373 | −0.002 | −0.328 | 0.318 |
| Col1a1 | −0.415 | −0.428 | −0.304 | −0.538 | −0.381 | −0.528 |
| Lgals1 | 0.195 | −0.116 | 0.408 | −0.085 | 0.302 | −0.511 |
| Arpc1b | −0.301 | −0.924 | 0.248 | −0.267 | 0.827 | 0.040 |
| CD53 | −0.105 | −0.427 | −0.300 | −0.158 | 1.111 | −0.328 |
| Itgb2 | −0.136 | −0.151 | −0.247 | −0.103 | 1.160 | 0.227 |
| Itga1 | 0.059 | 0.355 | −0.093 | −0.412 | 1.447 | −0.281 |
| RT1-Da | 0.099 | 0.161 | −0.167 | −0.931 | 1.985 | −0.486 |
| Lgals3bp | 0.056 | 0.102 | −0.162 | −0.294 | 0.062 | −0.716 |
| Pcolce | 0.015 | 0.196 | 0.073 | 0.076 | 2.330 | 0.426 |
| CP | −0.042 | 0.291 | 0.177 | 0.040 | 1.368 | 0.311 |
| Igfbp2 | −0.709 | −0.193 | 0.599 | −0.195 | 0.598 | −0.446 |
| CD9 | −0.059 | −0.017 | −0.191 | −0.428 | 0.167 | 0.165 |
| Serpine1 | 0.011 | −0.268 | 0.380 | 0.106 | 0.059 | −0.011 |
| Lox | −0.046 | −0.307 | −0.417 | −1.068 | −0.751 | −0.389 |
| Plod2 | −0.017 | −0.688 | −0.114 | 0.043 | −0.133 | −0.051 |
| Plat | 0.253 | 0.316 | −0.282 | 0.547 | −0.406 | −0.391 |
| Slc25a24 | −0.024 | −0.030 | 0.255 | −0.095 | 0.475 | 0.259 |
| Fam102b | −0.141 | 0.241 | −0.019 | −0.150 | 0.888 | −0.037 |
| Col1a2 | −0.128 | 0.532 | −0.168 | −0.376 | −0.465 | 0.123 |
| Fxyd5 | −0.207 | 0.189 | 0.132 | 0.174 | 0.732 | −0.097 |
| Fam105a | −0.534 | −0.152 | −0.021 | −0.045 | 1.055 | −0.053 |
| Timp1 | 0.325 | −0.176 | 0.366 | 0.088 | 0.977 | 0.347 |
| S100A6 | 0.360 | 0.429 | 0.376 | −0.573 | 0.477 | −0.258 |
| Lgals3 | −0.691 | −0.093 | −0.130 | −0.298 | 1.429 | −0.491 |
| Gpnmb | 0.657 | 0.046 | 0.471 | −0.359 | 1.697 | 0.355 |
| Anxa2 | 0.042 | 0.046 | 0.355 | −0.234 | 0.538 | −0.257 |
| Lum | −0.995 | 1.310 | 1.223 | 0.281 | 1.134 | −0.094 |
| Mmp2 | 0.032 | 0.399 | 0.286 | −0.110 | −0.695 | 0.179 |
| Igfbp1 | −0.367 | 0.547 | 0.145 | −0.001 | −0.502 | 0.821 |
| Cyp2c11 | 0.168 | −0.007 | −0.189 | −0.144 | −1.921 | 0.345 |
| Angptl3 | 0.025 | 0.210 | 0.028 | −0.047 | −0.527 | 0.050 |
| Apoc | 0.149 | 0.028 | 0.036 | −0.195 | −0.218 | 0.314 |
| Vtn | 0.102 | 0.047 | −0.095 | −0.125 | −0.089 | 0.237 |
| Tgfb1 | −0.071 | 0.315 | −0.026 | −0.081 | −0.570 | 0.065 |
| Igfbp3 | −0.332 | 0.014 | −0.077 | −0.824 | −1.372 | −0.157 |
| Cxcl12 | −0.257 | 0.230 | −0.373 | −0.298 | −0.774 | −0.028 |
| Igfals | 0.197 | −0.459 | −0.445 | −0.061 | −0.832 | −0.816 |
| Serping1 | −0.133 | 0.240 | −0.232 | 0.002 | 0.553 | 0.220 |
| Fn1 | 0.210 | 0.139 | −0.134 | −0.059 | −0.170 | 0.198 |
| Lrp1 | 0.187 | 0.232 | 0.132 | 0.020 | 0.071 | 0.447 |

TABLE 2-continued

Differential Expression of Genes in Rats After Exposure to Toxicants

| Animal Number | 17 | 18 | 20 | 93 | 94 | 95 |
|---|---|---|---|---|---|---|
| Toxicant | Allyl Alcohol | Allyl Alcohol | Allyl Alcohol | 4,4'-MDA | 4,4'-MDA | 4,4'-MDA |
| Dose (mg/kg) | 45 | 45 | 45 | 59.7 | 59.7 | 59.7 |
| Inflammation | 3 | 3 | 2 | 2 | 2 | 3 |
| Vacuolation| | 0 | 0 | 0 | 0 | 0 | 0 |
| Bile Duct Hyperplasia and Fibroplasia | 3 | 3 | 3 | 2 | 3 | 2 |
| Cytoplasmic Alteration | 3 | 4 | 2 | 4 | 3 | 3 |
| Necrosis | 3 | 4 | 3 | 1 | 0 | 1 |
| Gapdh | 2361.3 | 29950.5 | 2307.8 | 2384 | 3133 | 2922.5 |
| Hprt1 | 547.5 | 896.8 | 740 | 1089.8 | 1052.3 | 1451 |
| Ppib | 1372.8 | 2253.5 | 1995.8 | 1414.8 | 1548.8 | 1852 |
| A2m | −0.580 | 4.275 | −1.491 | −0.640 | −0.558 | 1.003 |
| Cxcl1 | 0.709 | 1.478 | 0.732 | 0.006 | 1.807 | 1.403 |
| RT1-DMa | −0.179 | 1.566 | 0.265 | 1.381 | 2.022 | 2.522 |
| Arf6 | −0.256 | 0.178 | −0.132 | 0.149 | 0.370 | 0.269 |
| Dsc2 | −0.171 | 0.507 | 0.455 | 0.258 | 0.244 | 0.474 |
| Sod2 | −0.161 | −0.460 | −0.493 | −0.094 | 0.474 | 0.238 |
| Cxcl16 | −1.080 | −0.133 | −1.040 | 1.969 | 1.196 | 2.174 |
| Lamc2 | −0.663 | −0.451 | −0.829 | 1.485 | 0.755 | 1.416 |
| Ccl2 | −0.383 | 0.979 | −0.393 | 1.483 | 1.928 | 1.705 |
| Col5a2 | −0.380 | 1.284 | −0.148 | 0.887 | 0.265 | 0.427 |
| Arrb1 | −0.740 | −0.404 | −0.991 | 1.051 | 0.640 | 0.525 |
| Vhl | −0.599 | −0.718 | −0.760 | 0.631 | 0.018 | −0.164 |
| Ctgf | 0.129 | 0.280 | −1.205 | 1.026 | 0.691 | 1.013 |
| Lcn2 | 0.971 | 1.169 | 6.080 | 4.000 | 3.904 | −1.530 |
| Lbp | 0.361 | 3.078 | 2.165 | 2.023 | 1.422 | 2.026 |
| S100A11 | −0.212 | 2.960 | 0.779 | 2.239 | 1.096 | 2.659 |
| Pkm2 | 0.103 | 2.906 | 0.739 | 1.314 | 1.491 | 2.389 |
| Tagln2 | −0.062 | 2.063 | 0.679 | 1.404 | 1.169 | 1.971 |
| Cyba | −0.108 | 1.351 | 0.399 | 1.216 | 1.165 | 2.041 |
| Capg | −0.205 | 1.938 | 0.402 | 1.169 | 1.723 | 2.026 |
| C1qb | 0.144 | 1.031 | 0.458 | 0.893 | 0.937 | 1.469 |
| Plau | −0.162 | 1.311 | 0.183 | 0.941 | 0.957 | 1.332 |
| Fstl1 | −0.366 | 0.758 | 0.206 | 0.146 | −0.373 | 0.049 |
| Vim | 0.242 | 2.666 | 0.914 | 0.931 | 0.440 | 1.584 |
| Col4a1 | 0.229 | 1.380 | 0.191 | 0.698 | 0.058 | 0.684 |
| Fbn1 | −0.189 | 1.419 | −0.456 | 0.719 | −0.043 | 0.697 |
| Nid1 | −0.377 | 1.359 | 0.495 | 0.747 | 0.101 | 0.465 |
| Col1a1 | 0.086 | 3.691 | 0.327 | 2.154 | 0.097 | 2.194 |
| Lgals1 | −0.189 | 3.063 | 0.892 | 1.636 | 0.107 | 1.896 |
| Arpc1b | −0.388 | 1.059 | 0.091 | 1.147 | 1.069 | 1.373 |
| CD53 | −0.329 | 0.597 | −0.343 | 0.950 | 1.045 | 1.560 |
| Itgb2 | −0.060 | 0.983 | 0.101 | 0.709 | 1.138 | 1.216 |
| Itga1 | −0.051 | 0.894 | 0.230 | 1.064 | 1.196 | 1.743 |
| RT1-Da | −0.957 | −1.800 | −0.732 | 1.431 | 2.375 | 2.640 |
| Lgals3bp | −0.162 | 0.589 | −0.332 | 0.425 | −0.042 | 0.829 |
| Pcolce | 0.539 | 3.259 | 2.844 | 0.994 | 0.041 | 1.107 |
| CP | 0.143 | 0.367 | 0.647 | 0.813 | 0.264 | 0.806 |
| Igfbp2 | −0.600 | 1.258 | 0.806 | 0.776 | −0.213 | 1.037 |
| CD9 | −0.024 | 1.780 | 0.219 | 1.728 | 0.138 | 1.640 |
| Serpine1 | −0.124 | 2.721 | 0.135 | 1.151 | 1.305 | 1.475 |
| Lox | −0.810 | 2.071 | 0.324 | 0.895 | −0.222 | 1.366 |
| Plod2 | −0.544 | 2.493 | 0.226 | 0.920 | 0.061 | 1.396 |
| Plat | −0.163 | 2.270 | 0.392 | 1.791 | 0.571 | 2.379 |
| Slc25a24 | −0.100 | 1.023 | 0.557 | 0.681 | 0.370 | 0.863 |
| Fam102b | −0.248 | 0.903 | 0.026 | 0.577 | 0.939 | 0.845 |
| Col1a2 | −0.226 | 2.322 | −0.358 | 0.966 | −0.355 | 0.902 |
| Fxyd5 | 0.027 | 2.267 | 0.487 | 1.025 | 0.916 | 1.613 |
| Fam105a | 0.114 | 1.529 | 0.324 | 1.236 | 1.186 | 1.900 |
| Timp1 | 0.025 | 3.024 | 1.159 | 1.871 | 1.153 | 2.099 |
| S100A6 | 0.290 | 2.362 | 1.807 | 0.965 | −0.038 | 1.228 |
| Lgals3 | 0.123 | 2.958 | 1.249 | 1.931 | 2.085 | 2.575 |
| Gpnmb | 0.340 | 3.532 | 0.925 | 1.876 | 1.911 | 3.162 |
| Anxa2 | 0.755 | 2.785 | 1.558 | 2.439 | 1.755 | 2.514 |
| Lum | −0.063 | 3.392 | −0.236 | −1.037 | −0.339 | 0.558 |
| Mmp2 | −0.333 | 1.189 | −0.434 | −0.171 | −1.012 | −0.273 |
| Igfbp1 | 0.221 | 1.272 | −0.858 | −0.300 | −0.689 | −0.424 |
| Cyp2c11 | 0.027 | −7.636 | −5.217 | −4.496 | −0.998 | −2.003 |
| Angptl3 | 0.071 | −1.620 | −0.819 | −1.342 | −1.123 | −1.335 |
| Apoc | −0.016 | −1.114 | −0.462 | −0.246 | −0.561 | −0.801 |
| Vtn | 0.017 | −1.150 | −0.324 | −0.546 | −0.532 | −0.859 |
| Tgfb1 | −0.395 | −0.983 | −0.515 | −0.639 | −0.667 | −0.942 |
| Igfbp3 | −0.979 | −1.769 | −1.970 | −2.961 | −1.352 | −2.494 |
| Cxcl12 | −0.990 | −1.586 | −1.327 | −1.347 | −1.272 | −2.109 |
| Igfals | −0.880 | −2.148 | −0.970 | −0.785 | −0.893 | −1.298 |

TABLE 2-continued

Differential Expression of Genes in Rats After Exposure to Toxicants

| | | | | | | |
|---|---|---|---|---|---|---|
| Serping1 | −0.218 | −0.498 | −0.370 | −0.220 | −0.023 | 0.055 |
| Fn1 | −0.486 | −0.195 | −0.420 | −0.390 | −0.812 | −0.766 |
| Lrp1 | −0.300 | −0.419 | −0.347 | −0.452 | −0.348 | −0.613 |
| Animal Number | 96 | 97 | 98 | 99 | 100 | 54 |
| Toxicant | 4,4'-MDA | 4,4'-MDA | 4,4'-MDA | 4,4'-MDA | 4,4'-MDA | Carbon Tetrachloride |
| Dose (mg/kg) | 59.7 | 162 | 162 | 162 | 162 | 200 |
| Inflammation | 2 | 2 | 2 | 2 | 2 | 0 |
| Vacuolation | 0 | 0 | 0 | 0 | 0 | 3 |
| Bile Duct Hyperplasia and Fibroplasia | 2 | 3 | 2 | 3 | 3 | 0 |
| Cytoplasmic Alteration | 1 | 2 | 3 | 2 | 3 | 0 |
| Necrosis | 1 | 2 | 2 | 2 | 1 | 1 |
| Gapdh | 2508 | 2700.5 | 2891.3 | 2103.5 | 2272 | 2379.5 |
| Hprt1 | 2073.5 | 2119.3 | 2624 | 1897.8 | 2070.5 | 569 |
| Ppib | 1909.5 | 1795.8 | 2013.5 | 1461 | 1412.5 | 1274.8 |
| A2m | −0.515 | −0.752 | −0.367 | 0.636 | −0.146 | −3.423 |
| Cxcl1 | 1.052 | 1.645 | 2.036 | 2.699 | 1.178 | 0.190 |
| RT1-DMa | 1.938 | 1.970 | 1.713 | 2.157 | 1.814 | 0.225 |
| Arf6 | 0.145 | −0.012 | −0.034 | 0.104 | 0.197 | 0.270 |
| Dsc2 | 0.455 | 0.394 | 0.678 | 0.955 | 0.720 | 0.091 |
| Sod2 | 0.257 | 0.336 | 0.432 | 0.612 | 0.168 | 0.022 |
| Cxcl16 | 2.503 | 2.029 | 2.368 | 2.877 | 2.768 | 1.440 |
| Lame2 | 1.029 | 0.703 | 0.793 | 0.530 | 1.041 | 2.323 |
| Ccl2 | 1.065 | 1.491 | 1.899 | 1.638 | 2.340 | 1.671 |
| Col5a2 | −0.015 | −0.359 | 0.858 | 0.442 | 0.935 | 1.411 |
| Arrb1 | 0.108 | −0.641 | 0.602 | 0.081 | 0.761 | 1.846 |
| Vhl | −1.077 | −1.397 | −0.595 | −1.062 | −0.377 | 2.369 |
| Ctgf | 0.905 | 1.758 | 2.136 | 1.451 | 1.889 | 2.135 |
| Lcn2 | 3.180 | 3.402 | 4.407 | 4.653 | 3.803 | −1.654 |
| Lbp | 2.387 | 2.111 | 2.928 | 2.713 | 2.458 | 0.594 |
| S100A11 | 2.619 | 2.033 | 2.948 | 2.479 | 3.288 | 0.119 |
| Pkm2 | 1.504 | 1.650 | 1.865 | 1.904 | 2.017 | 0.077 |
| Tagln2 | 1.740 | 1.605 | 1.734 | 1.682 | 2.383 | 0.218 |
| Cyba | 1.810 | 2.010 | 1.548 | 1.991 | 1.782 | 0.522 |
| Capg | 1.532 | 1.814 | 1.658 | 1.581 | 1.640 | 0.433 |
| C1qb | 1.301 | 1.519 | 1.224 | 1.246 | 1.125 | 0.268 |
| Plau | 0.619 | 1.177 | 1.067 | 0.958 | 1.279 | 0.039 |
| Fstl1 | −0.119 | −0.341 | 0.583 | 0.306 | 0.474 | −0.259 |
| Vim | 1.307 | 1.272 | 1.805 | 1.565 | 1.565 | 0.044 |
| Col4a1 | 0.585 | 0.211 | 1.119 | 1.046 | 1.114 | −0.521 |
| Fbn1 | 0.605 | 0.275 | 1.122 | 1.128 | 1.175 | −0.149 |
| Nid1 | 0.461 | 0.170 | 0.761 | 0.787 | 0.844 | −0.021 |
| Col1a1 | 2.326 | 1.772 | 2.933 | 3.350 | 2.716 | 1.336 |
| Lgals1 | 1.858 | 1.032 | 2.647 | 1.699 | 2.117 | 0.936 |
| Arpc1b | 1.030 | 0.946 | 1.048 | 0.964 | 1.356 | 1.102 |
| CD53 | 0.774 | 1.175 | 0.819 | 0.838 | 0.720 | 0.486 |
| Itgb2 | 0.694 | 0.886 | 0.789 | 0.754 | 0.987 | −0.115 |
| Itga1 | 1.001 | 1.202 | 0.739 | 0.951 | 0.883 | 0.220 |
| RT1-Da | 1.941 | 2.321 | 1.129 | 2.013 | 1.586 | 0.559 |
| Lgals3bp | 0.713 | 0.544 | 0.531 | 0.265 | 0.276 | 0.391 |
| Pcolce | 1.109 | 0.772 | 1.597 | 1.301 | 1.175 | 0.002 |
| CP | 0.697 | 0.445 | 0.674 | 1.008 | 0.437 | −0.227 |
| Igfbp2 | 0.901 | 1.443 | 1.840 | 1.128 | 1.008 | −0.542 |
| CD9 | 2.055 | 1.358 | 2.688 | 2.147 | 2.614 | −0.279 |
| Serpine1 | 2.110 | 2.887 | 3.371 | 2.709 | 3.163 | 0.309 |
| Lox | 1.400 | 0.880 | 2.251 | 1.957 | 1.785 | −0.215 |
| Plod2 | 0.943 | 0.699 | 1.892 | 1.531 | 1.735 | −0.129 |
| Plat | 2.086 | 1.548 | 2.206 | 1.733 | 2.853 | −0.025 |
| Slc25a24 | 0.633 | 0.633 | 1.136 | 0.805 | 1.373 | −0.245 |
| Fam102b | 0.833 | 0.111 | 0.705 | 0.848 | 1.119 | −0.378 |
| Col1a2 | 0.998 | 0.413 | 1.187 | 1.817 | 1.005 | 0.249 |
| Fxyd5 | 1.315 | 1.096 | 1.541 | 1.448 | 1.502 | 0.160 |
| Fam105a | 1.417 | 1.449 | 1.702 | 1.583 | 1.587 | 0.309 |
| Timp1 | 1.999 | 1.521 | 2.473 | 1.865 | 2.263 | 0.939 |
| S100A6 | 1.292 | 0.849 | 2.063 | 1.331 | 1.619 | −0.079 |
| Lgals3 | 2.499 | 2.803 | 2.873 | 2.782 | 2.940 | 0.994 |
| Gpnmb | 2.992 | 3.525 | 3.032 | 3.519 | 2.971 | 1.494 |
| Anxa2 | 2.736 | 2.105 | 2.876 | 2.212 | 2.902 | 0.553 |
| Lum | 0.802 | −1.943 | 0.958 | −0.269 | 1.679 | 0.298 |
| Mmp2 | −0.386 | −0.485 | −0.564 | −0.428 | −0.503 | −0.062 |
| Igfbp1 | 0.366 | 1.713 | 0.883 | −0.527 | 0.382 | 0.019 |
| Cyp2c11 | −3.316 | −4.316 | −7.665 | −5.415 | −6.029 | −1.357 |
| Angptl3 | −1.715 | −1.877 | −2.329 | −1.959 | −2.302 | −0.612 |
| Apoc | −0.672 | −0.874 | −1.118 | −0.549 | −1.212 | −0.311 |
| Vtn | −0.983 | −1.300 | −1.045 | −0.963 | −1.331 | −0.291 |

TABLE 2-continued

Differential Expression of Genes in Rats After Exposure to Toxicants

| | | | | | | |
|---|---|---|---|---|---|---|
| Tgfb1 | −1.056 | −1.330 | −1.371 | −1.473 | −1.298 | −0.322 |
| Igfbp3 | −3.956 | −3.946 | −3.678 | −3.158 | −3.073 | −0.324 |
| Cxcl12 | −2.203 | −2.321 | −2.314 | −2.944 | −2.233 | 0.040 |
| Igfals | −1.423 | −1.560 | −1.580 | −1.254 | −1.386 | −0.528 |
| Serping1 | −0.287 | −0.559 | −0.476 | −0.077 | −0.527 | −0.712 |
| Fn1 | −0.524 | −1.030 | −0.711 | −0.869 | −0.680 | −0.120 |
| Lrp1 | −0.638 | −0.730 | −0.779 | −0.663 | −0.837 | −0.329 |

| Animal Number | 46 | 47 | 48 | 37 | 38 | 39 |
|---|---|---|---|---|---|---|
| Toxicant | Carbon Tetrachloride | Carbon Tetrachloride | Carbon Tetrachloride | Bromobenzene | Bromobenzene | Bromobenzene |
| Dose (mg/kg) | 200 | 200 | 200 | 785 | 785 | 785 |
| Inflammation | 0 | 0 | 0 | 1 | 1 | 2 |
| Vacuolation | 4 | 3 | 3 | 2 | 3 | 3 |
| Bile Duct Hyperplasia and Fibroplasia | 0 | 0 | 0 | 0 | 0 | 0 |
| Cytoplasmic Alteration | 0 | 1 | 2 | 1 | 2 | 3 |
| Necrosis | 1 | 0 | 1 | 0 | 0 | 3 |
| Gapdh | 2608 | 2613.3 | 2661.3 | 2931.8 | 2799.3 | 2968.3 |
| Hprt1 | 735.3 | 656 | 561.5 | 1715 | 1739.5 | 1380 |
| Ppib | 1972.8 | 1801.5 | 1853.8 | 1675.5 | 1900 | 1655.3 |
| A2m | −2.891 | −2.439 | −5.167 | −4.054 | −4.444 | −2.844 |
| Cxcl1 | −0.500 | −0.165 | −0.462 | −0.610 | −0.492 | −0.386 |
| RT1-DMa | 0.711 | 0.673 | 1.089 | −0.569 | −0.589 | 0.149 |
| Arf6 | 0.172 | 0.167 | 0.214 | 0.324 | 0.475 | 0.461 |
| Dsc2 | −0.280 | −0.204 | −0.265 | 0.800 | 0.827 | 0.610 |
| Sod2 | 0.009 | −0.014 | −0.116 | 0.200 | −0.035 | 0.134 |
| Cxcl16 | 1.782 | 1.992 | 1.656 | −0.140 | −1.150 | −0.275 |
| Lamc2 | 2.130 | 2.338 | 1.341 | −0.725 | −1.692 | −0.854 |
| Ccl2 | 1.662 | 2.378 | 1.370 | −0.790 | −1.244 | −1.328 |
| Col5a2 | 2.330 | 2.442 | 2.138 | −0.708 | −0.778 | −0.542 |
| Arrb1 | 2.288 | 2.226 | 1.692 | −1.220 | −1.482 | −0.627 |
| Vhl | 2.626 | 2.628 | 2.130 | 0.043 | −0.096 | −0.334 |
| Ctgf | 2.232 | 2.664 | 1.663 | −1.387 | −1.037 | −0.649 |
| Lcn2 | 0.356 | 1.528 | 2.126 | −0.682 | −0.719 | −0.661 |
| Lbp | 0.379 | 0.665 | 0.050 | 0.157 | 0.036 | 0.207 |
| S100A11 | 0.421 | 0.731 | 0.599 | −0.356 | −0.292 | 0.061 |
| Pkm2 | 0.586 | 0.642 | 0.663 | −0.142 | −0.085 | 0.069 |
| Tagln2 | 0.282 | 0.110 | 0.153 | −0.669 | −0.625 | 0.147 |
| Cyba | 0.799 | 0.888 | 0.887 | −0.761 | −0.590 | 0.049 |
| Capg | 0.855 | 0.909 | 0.968 | −0.835 | −0.762 | 0.053 |
| C1qb | 0.290 | 0.085 | 0.332 | −0.465 | −0.014 | 0.309 |
| Plau | 0.765 | 0.947 | 0.720 | −1.049 | −0.402 | −0.470 |
| Fstl1 | 0.017 | −0.180 | 0.025 | −1.078 | −0.899 | −0.423 |
| Vim | 0.004 | 0.348 | 0.360 | −0.148 | −0.045 | −0.109 |
| Col4a1 | −0.024 | −0.441 | 0.104 | −0.512 | −0.387 | −0.163 |
| Fbn1 | 0.230 | −0.294 | 0.107 | −1.303 | −1.090 | −0.632 |
| Nid1 | 0.232 | 0.186 | 0.154 | −0.460 | −0.132 | 0.014 |
| Col1a1 | 1.411 | 1.309 | 1.774 | −0.659 | −0.336 | 0.149 |
| Lgals1 | 0.978 | 1.986 | 1.602 | −0.856 | −0.388 | −0.455 |
| Arpc1b | 1.145 | 1.554 | 1.382 | −0.171 | −0.454 | −0.337 |
| CD53 | 1.094 | 1.315 | 1.262 | −0.045 | −0.339 | 0.303 |
| Itgb2 | 0.502 | 0.455 | 0.302 | −0.722 | −0.914 | −0.301 |
| Itga1 | 0.585 | 0.503 | 0.756 | −0.672 | −0.525 | 0.257 |
| RT1-Da | 0.918 | 1.213 | 1.280 | −0.205 | −0.563 | 0.533 |
| Lgals3bp | 0.486 | 0.360 | 0.302 | −0.415 | −0.105 | 0.126 |
| Pcolce | 0.354 | 0.651 | −0.401 | −1.230 | −0.974 | −0.145 |
| CP | −0.328 | −0.317 | −0.414 | −1.055 | −0.969 | −0.530 |
| Igfbp2 | 1.416 | 0.505 | −1.839 | 0.339 | 0.249 | −0.180 |
| CD9 | −0.103 | 0.754 | −0.347 | −0.072 | −0.052 | 0.416 |
| Serpine1 | −0.345 | 0.467 | −0.524 | 0.153 | 0.825 | −0.550 |
| Lox | −0.493 | 0.022 | 0.077 | −1.197 | −1.023 | −0.699 |
| Plod2 | −0.357 | −0.045 | −0.258 | −0.446 | −0.410 | −0.613 |
| Plat | −0.411 | −0.289 | −0.385 | 0.202 | 0.005 | 0.027 |
| Slc25a24 | −0.511 | −0.262 | −0.615 | −0.143 | 0.149 | 0.189 |
| Fam102b | −0.140 | −0.011 | −0.240 | −0.808 | −0.338 | −0.148 |
| Col1a2 | 0.458 | 0.329 | 0.672 | −0.901 | −0.686 | −0.378 |
| Fxyd5 | 0.404 | 0.507 | 0.213 | −0.189 | −0.159 | 0.283 |
| Fam105a | 0.576 | 0.985 | 0.758 | −0.461 | −0.047 | 0.188 |
| Timp1 | 1.200 | 1.645 | 1.241 | −0.428 | −0.191 | −0.231 |
| S100A6 | −0.686 | 0.408 | −0.019 | −0.521 | 0.005 | −0.682 |
| Lgals3 | 1.444 | 2.024 | 1.736 | 1.367 | 0.936 | 1.432 |
| Gpnmb | 2.232 | 3.101 | 2.714 | 1.906 | 1.987 | 2.373 |
| Anxa2 | 0.586 | 0.834 | 0.587 | 1.771 | 1.226 | 1.391 |
| Lum | −0.201 | 0.404 | 0.442 | −0.152 | −0.296 | −0.116 |
| Mmp2 | 0.311 | 0.610 | −0.241 | −0.086 | 0.177 | 0.235 |
| Igfbp1 | 0.070 | 0.480 | −0.925 | 3.275 | 3.897 | 0.758 |

TABLE 2-continued

Differential Expression of Genes in Rats After Exposure to Toxicants

| | | | | | |
|---|---|---|---|---|---|
| Cyp2c11 | −3.301 | −0.339 | −0.904 | −7.760 | −8.696 | −7.411 |
| Angptl3 | −1.071 | −0.753 | −0.775 | −0.864 | −1.104 | −0.499 |
| Apoc | −0.356 | −0.337 | −0.414 | −0.325 | −0.372 | −0.172 |
| Vtn | −0.381 | −0.494 | −0.473 | −1.353 | −1.261 | −0.746 |
| Tgfb1 | 0.107 | −0.102 | −0.395 | −0.596 | −0.528 | −0.330 |
| Igfbp3 | 0.063 | −0.304 | −0.113 | −2.127 | −1.911 | −1.316 |
| Cxcl12 | 0.320 | 0.041 | 0.403 | −2.564 | −2.540 | −1.640 |
| Igfals | −0.092 | −0.771 | −0.189 | −2.524 | −2.336 | −2.083 |
| Serping1 | −0.714 | −0.546 | −0.514 | −1.107 | −0.925 | −0.627 |
| Fn1 | −0.152 | −0.364 | −0.262 | −1.880 | −1.522 | −1.313 |
| Lrp1 | −0.337 | −0.524 | −0.671 | −1.297 | −1.003 | −0.323 |

| Animal Number | 40 | 65 | 66 | 67 | 68 |
|---|---|---|---|---|---|
| Toxicant | Bromobenzene | Dexamethasone | Dexamethasone | Dexamethasone | Dexamethasone |
| Dose (mg/kg) | 785 | 1 | 1 | 1 | 1 |
| Inflammation | 1 | 0 | 0 | 0 | 0 |
| Vacuolation | 1 | 0 | 0 | 0 | 0 |
| Bile Duct Hyperplasia and Fibroplasia | 0 | 0 | 0 | 0 | 0 |
| Cytoplasmic Alteration | 1 | 4 | 4 | 4 | 4 |
| Necrosis | 0 | 1 | 1 | 1 | 3 |
| Gapdh | 2811 | 2151.5 | 1813.3 | 2471 | 3013.3 |
| Hprt1 | 1716 | 324.3 | 278.5 | 478.5 | 537.5 |
| Ppib | 1677.3 | 1332.3 | 982.3 | 1040 | 1524.8 |
| A2m | −1.670 | −1.370 | −0.649 | −0.615 | −0.252 |
| Cxcl1 | −0.930 | 0.104 | 1.127 | 0.364 | 0.097 |
| RT1-DMa | −0.606 | 3.152 | 2.497 | 3.371 | 2.417 |
| Arf6 | 0.239 | −0.268 | −0.346 | −0.401 | 0.005 |
| Dsc2 | 0.624 | −0.209 | −0.593 | −0.466 | −0.248 |
| Sod2 | 0.187 | −0.398 | −0.428 | −0.371 | −0.367 |
| Cxcl16 | −0.468 | −0.555 | −0.537 | −4.885 | 0.714 |
| Lame2 | −1.188 | −0.132 | 0.260 | −1.038 | 0.536 |
| Ccl2 | −1.622 | −0.272 | 0.250 | 0.043 | 1.019 |
| Col5a2 | −0.877 | −0.407 | −0.910 | −2.382 | 0.311 |
| Arrb1 | −2.254 | −0.840 | −2.152 | −3.043 | 0.703 |
| Vhl | −0.363 | −0.300 | −1.037 | −0.787 | 0.504 |
| Ctgf | −0.389 | −0.755 | 0.747 | −0.663 | 0.405 |
| Lcn2 | −1.007 | −0.470 | 0.418 | 0.883 | 0.535 |
| Lbp | −0.066 | 0.344 | −0.042 | 0.261 | −0.020 |
| S100A11 | −0.441 | −0.377 | −0.570 | −0.732 | −0.465 |
| Pkm2 | −0.110 | −0.668 | −0.611 | −0.735 | −0.472 |
| Tagln2 | −0.816 | −0.486 | −0.918 | −0.563 | −0.566 |
| Cyba | −0.752 | −0.998 | −1.793 | −1.244 | −0.956 |
| Capg | −1.140 | −0.558 | −0.744 | −0.772 | −0.404 |
| C1qb | 0.018 | −0.174 | −0.655 | −0.257 | −0.222 |
| Plau | −1.553 | −0.719 | −2.088 | −1.424 | −0.095 |
| Fstl1 | −1.140 | −1.085 | −1.346 | −1.183 | −0.931 |
| Vim | −0.327 | −1.514 | −0.856 | −1.292 | −1.277 |
| Col4a1 | −0.340 | −1.039 | −1.035 | −1.397 | −0.880 |
| Fbn1 | −1.013 | −1.213 | −1.784 | −2.160 | −1.736 |
| Nid1 | −0.579 | −1.271 | −1.374 | −1.271 | −1.155 |
| Col1a1 | −0.231 | −4.640 | −3.775 | −5.473 | −0.928 |
| Lgals1 | −0.084 | 0.458 | −4.140 | −0.346 | 0.583 |
| Arpc1b | −0.315 | −1.391 | −2.770 | −5.994 | −0.172 |
| CD53 | −0.440 | −0.716 | −3.901 | −5.862 | 0.006 |
| Itgb2 | −1.032 | −1.330 | −2.265 | −1.982 | −0.802 |
| Itga1 | −0.880 | −2.088 | −3.379 | −2.849 | −1.903 |
| RT1-Da | −0.554 | −4.927 | −7.563 | −4.272 | −3.443 |
| Lgals3bp | −0.427 | −1.477 | −0.782 | −1.281 | −0.669 |
| Pcolce | −1.087 | −1.293 | −1.196 | −1.572 | −0.246 |
| CP | −1.250 | −0.134 | −0.634 | −0.952 | −0.558 |
| Igfbp2 | 0.559 | −0.258 | −0.949 | −1.156 | −0.041 |
| CD9 | 0.476 | 0.155 | −0.656 | −0.280 | 0.387 |
| Serpine1 | 0.552 | 0.251 | 1.560 | 0.110 | 0.038 |
| Lox | −0.615 | 0.278 | 0.412 | −0.164 | 1.170 |
| Plod2 | −0.623 | −0.065 | 0.269 | −0.568 | −0.077 |
| Plat | 0.084 | 0.103 | 0.075 | −0.461 | −0.335 |
| Slc25a24 | −0.325 | −0.387 | −0.212 | −0.565 | −0.427 |
| Fam102b | −0.780 | −0.462 | −0.124 | −0.822 | −0.262 |
| Col1a2 | −0.731 | −0.960 | −1.057 | −2.208 | −1.081 |
| Fxyd5 | −0.184 | −0.247 | −0.412 | −0.151 | −0.305 |
| Fam105a | −0.207 | −0.295 | 0.195 | −0.809 | −0.294 |
| Timp1 | −0.056 | 0.026 | 0.464 | −0.134 | 1.004 |
| S100A6 | 0.207 | 0.650 | −0.047 | 0.843 | 0.695 |
| Lgals3 | 0.867 | 0.011 | 0.320 | 0.370 | 0.526 |
| Gpnmb | 1.454 | −0.018 | 1.304 | 0.968 | 1.447 |
| Anxa2 | 0.783 | 0.519 | 0.194 | −0.132 | 0.293 |

TABLE 2-continued

Differential Expression of Genes in Rats After Exposure to Toxicants

| Lum | −0.530 | 0.593 | 0.401 | −0.997 | −0.078 |
| Mmp2 | −0.151 | −0.245 | −1.273 | −0.990 | −0.583 |
| Igfbp1 | 3.616 | 1.132 | 1.740 | 0.780 | 0.489 |
| Cyp2c11 | −6.882 | 0.259 | 0.532 | −0.332 | 0.252 |
| Angptl3 | −0.518 | −0.276 | 0.029 | −0.467 | −0.241 |
| Apoc | −0.338 | −0.250 | −0.067 | −0.469 | −0.542 |
| Vtn | −0.854 | −0.111 | −0.294 | −0.579 | −0.572 |
| Tgfb1 | −0.639 | −1.193 | −1.526 | −1.328 | −1.429 |
| Igfbp3 | −1.713 | −1.125 | −1.454 | −2.523 | −1.663 |
| Cxcl12 | −2.717 | −1.808 | −3.742 | −2.144 | −1.869 |
| Igfals | −3.007 | −0.678 | −2.820 | −1.013 | −1.310 |
| Serping1 | −0.678 | 0.154 | 0.026 | −0.228 | 0.065 |
| Fn1 | −1.481 | 0.397 | 0.181 | −0.334 | −0.170 |
| Lrp1 | −1.011 | −0.206 | −0.631 | −0.863 | −0.371 |

Figure 7:
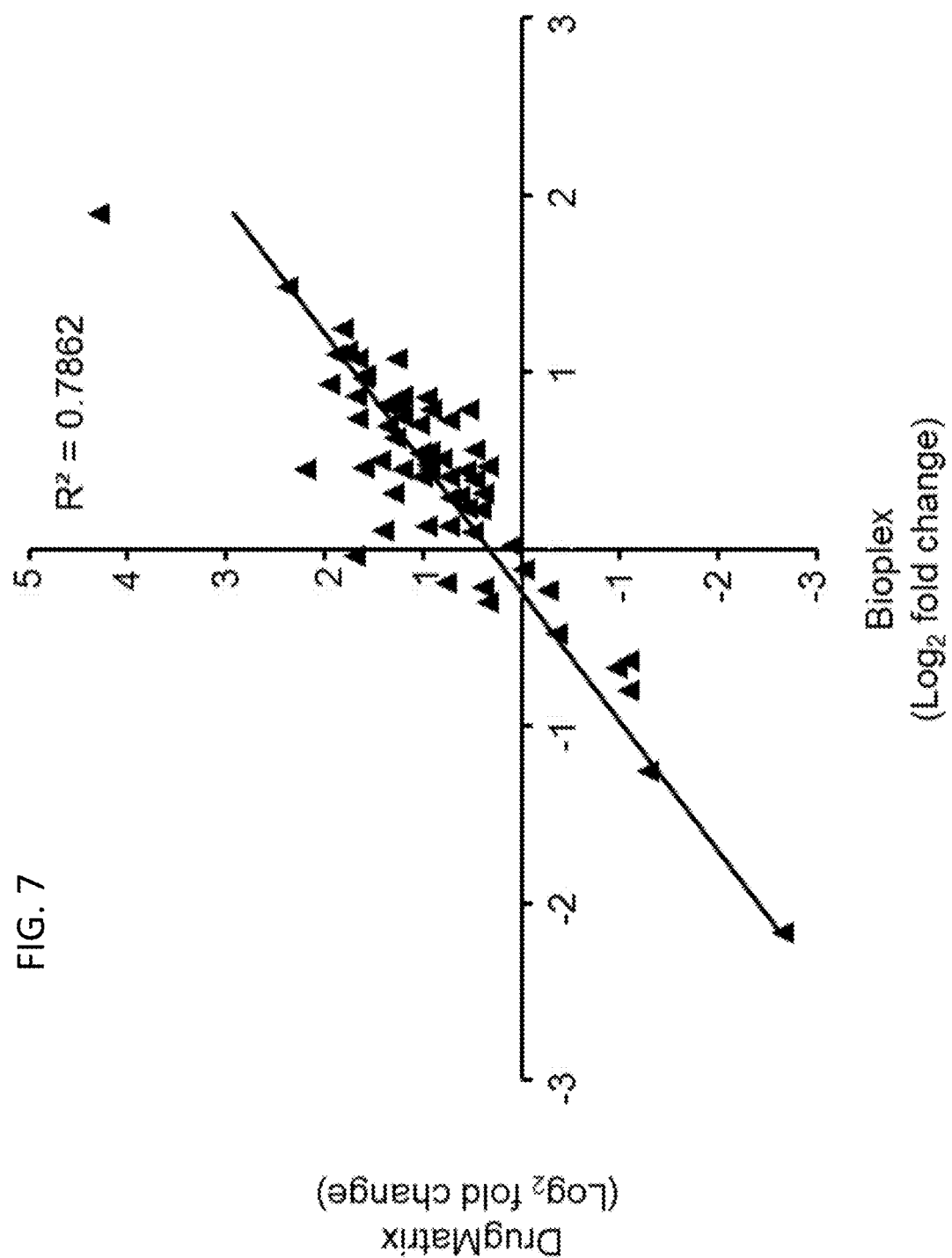
FIG. 7 exemplifies the positive correlation between liver $\log_2$ fold-changes in gene expression in data from DrugMatrix and the disclosed Bioplex data. A comparison of $\log_2$ fold-changes of panel genes using data from Drug Matrix with fold changes obtained with data from our multiplex experiments revealed a positive correlation ($R^2$=0.79). We used $\log_2$ fold-changes in gene panel expression associated with fibrogenic chemicals that show histopathological evidence of periportal or subcapsular fibrosis. Allyl alcohol, 4,4'-methylenedianiline, 1-naphthyl isothiocyanate, crotamiton, testosterone, carvedilol, carmustine, vinblastine, β-estradiol, and bezafibrate (5-7 days oral administration or intraperitoneal injection) at various doses scored fibrosis-positive in the DrugMatrix study. Allyl alcohol and 4,4'-methylenedianiline at high doses scored positive for fibrosis in the present study.

The expression patterns of the genes measured by the Bioplex multiplexed assay correlated positively with the expression patterns reported in the DrugMatrix database ($R2=0.79$; FIG. 7). The average log-ratio versus control across all samples showing fibrosis for genes on the Bioplex assay was well correlated with Drug Matrix.

Figure 8:
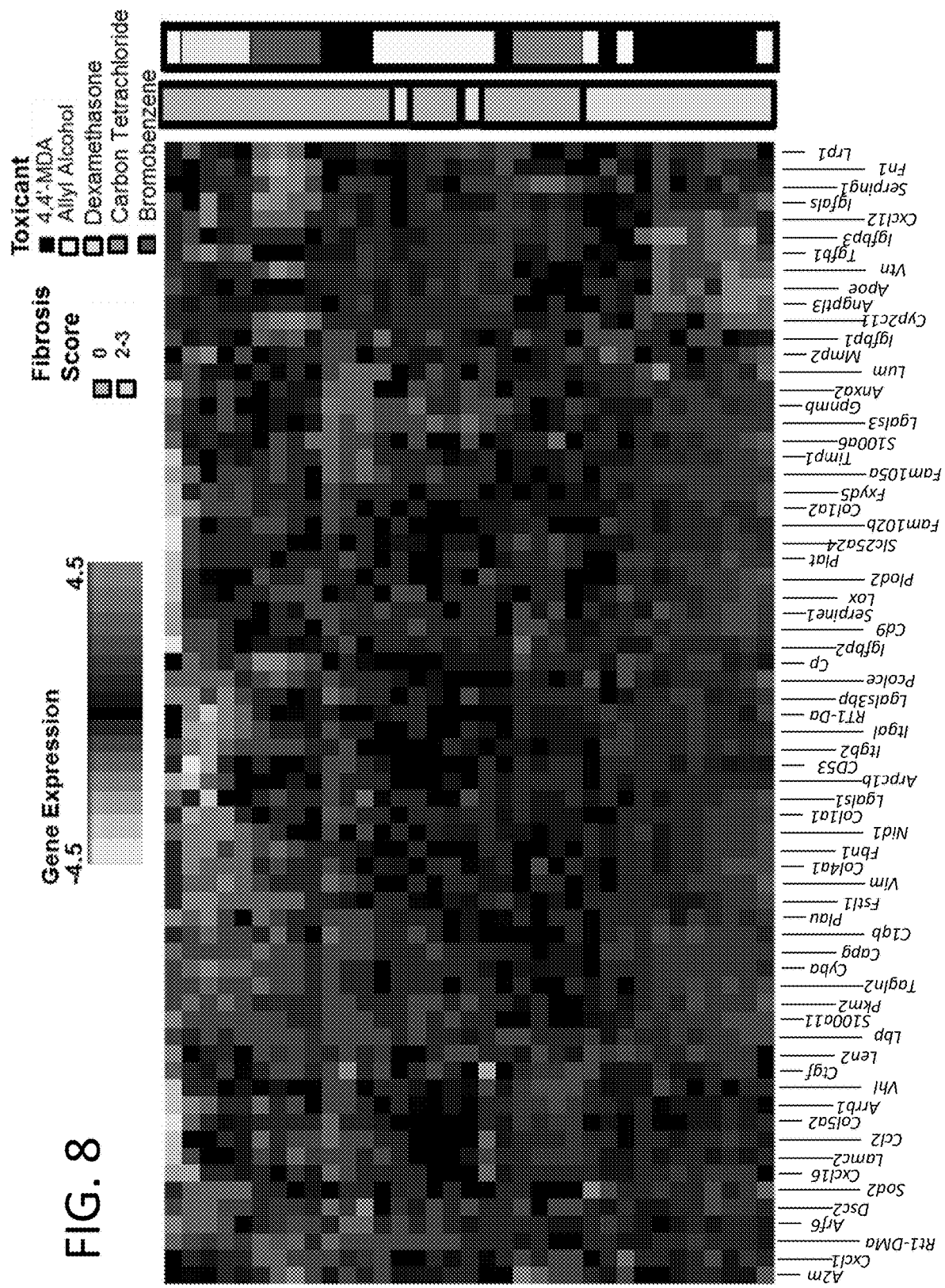
FIG. 8 exemplifies hierarchical biclustering of $\log_2$ fold-changes in gene expression patterns for 67 genes on the fibrosis gene panel in non-prefibrogenic and prefibrogenic pathologies. $\log_2$ fold-changes were determined for presumptive fibrosis gene indicators by multiplexed spectrophotometric Bioplex assay and visualized by hierarchical biclustering. 4,4'-MDA, 4,4'-methylenedianiline; 0-no observable pathology; 2-mild pathology (>30-60% of tissue affected); 3-moderate pathology (>60-80% of tissue affected). Data were standardized; the right side of the scale bar indicates higher expression relative to mean and the left side of the scale bar indicates lower expression relative to mean. The genes listed are in the same order as Table 1.

Differential gene expression was analyzed by hierarchical biclustering with the fibrogenic chemicals (all dose groups) (FIG. 8). Of the 67 genes available for analysis on the panel, fibrogenic chemicals causing fibrosis clustered separately on the y-axis, with the exception of two allyl alcohol-treated animals. Toxicant-dose groups with the fibrosis phenotype clustered separately from the vacuolation and glycogen accumulation phenotypes (FIG. 8). Carbon tetrachloride (the delayed-onset fibrogenic chemical) clustered mid-way between non-fibrogenic and fibrogenic doses of the other fibrogenic chemicals. Gene expression profiles for two allyl alcohol exposures with the fibrosis phenotype clustered with the non-fibrogenic chemical-dose groups. A third localized on the border between fibrogenic and nonfibrogenic clusters. All other fibrogenic chemical-dose groups with fibrosis clustered together. All of the fibrosis-positive animals dosed with 4,4'-methylenedianiline clustered together (FIG. 8).

Figure 9:
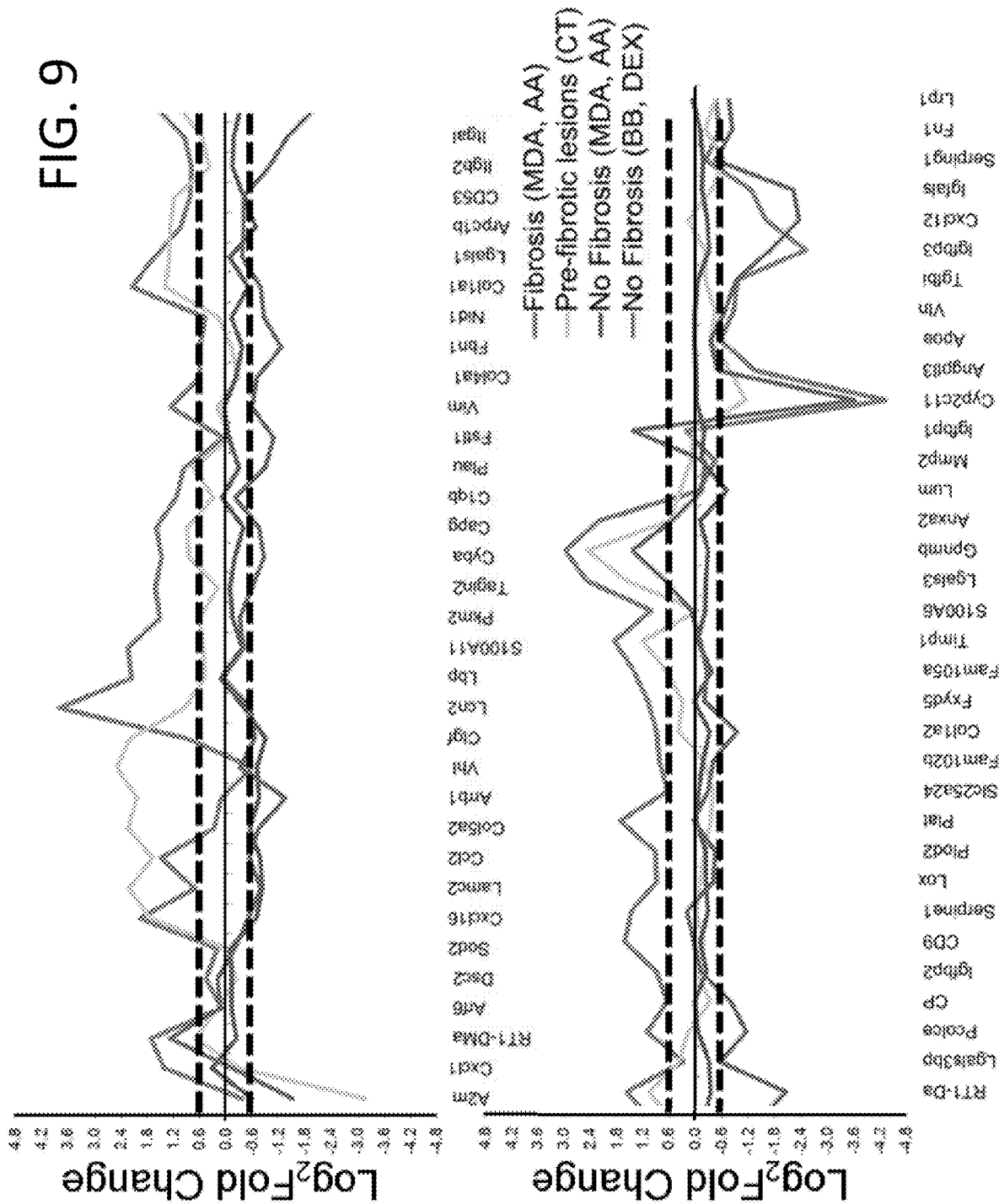
FIG. 9 exemplifies differentiable gene signature pattern for fibrogenic compounds with histopathological evidence of fibrosis. Expression ($\log_2$ fold-change over vehicle control) for 67 signature fibrogenic genes were plotted in order of the biclustering analysis (see FIG. 7 and Table 1). Bromobenzene, carbon tetrachloride, and dexamethasone exposures correlated with histopathological evidence of vacuolation and/or glyocgen accumulation [Nonfibrogenic Compounds, (Fibrosis−)]. High-dose 4,4'-methylenedianiline and allyl alcohol exposures were associated with fibrosis histopathology [Fibrogenic Compounds, (Fibrosis+)]. Low-dose 4,4'-methylenedianiline, allyl alcohol, and all doses of carbon tetrachloride were fibrogenic chemicals without fibrosis (Fibrosis−). Dashed lines represent the 1.5-fold threshold for significance.

Chemical-dose groups causing fibrosis produced more differential gene expression of the genes in the panel than chemical-dose groups without fibrosis (FIG. 9). The difference was most pronounced in upregulated genes (FIG. 9). For non-fibrogenic bromobenzene and dexamethasone, 12 genes were downregulated in the chemicals causing fatty accumulation profiles and upregulated in fibrogenic chemical-dose groups (>+1.5-fold [average] above dashed lines in FIG. 9 and Table 3; Col1a1, Col1a2, Col4a1, Cp, Cyba, Fbn1, Itgal, Itgb2, Pcolce, Plau, Lamac2, and RT1-Da). Of the 67 genes on the final panel, 19 were <+1.5-fold expression (FIG. 9; Table 2). Only one gene was significantly downregulated in the non-fibrosis chemical-dose group (A2m; a-2 macroglobulin). Expression of 51 out of the 67 genes (76% of the panel) was ±1.5-fold control expression for fibrogenic compounds with histopathological evidence of fibrosis (Table 2). Only one gene (1.5%) was +1.5-fold control expression for fibrogenic compounds without histopathological evidence of fibrosis (A2m). Panel gene expression of the carbon-tetrachloride dose group was midway between fibrosis-positive chemical-dose groups and non-fibrogenic chemical-dose groups (FIG. 9). Non-fibrogenic compounds induced differential expression in 33 out of the 67 genes (50% of the panel). Of these, expression was anti-correlated with fibrogenic, fibrosis-positive cohorts.

Figure 10:
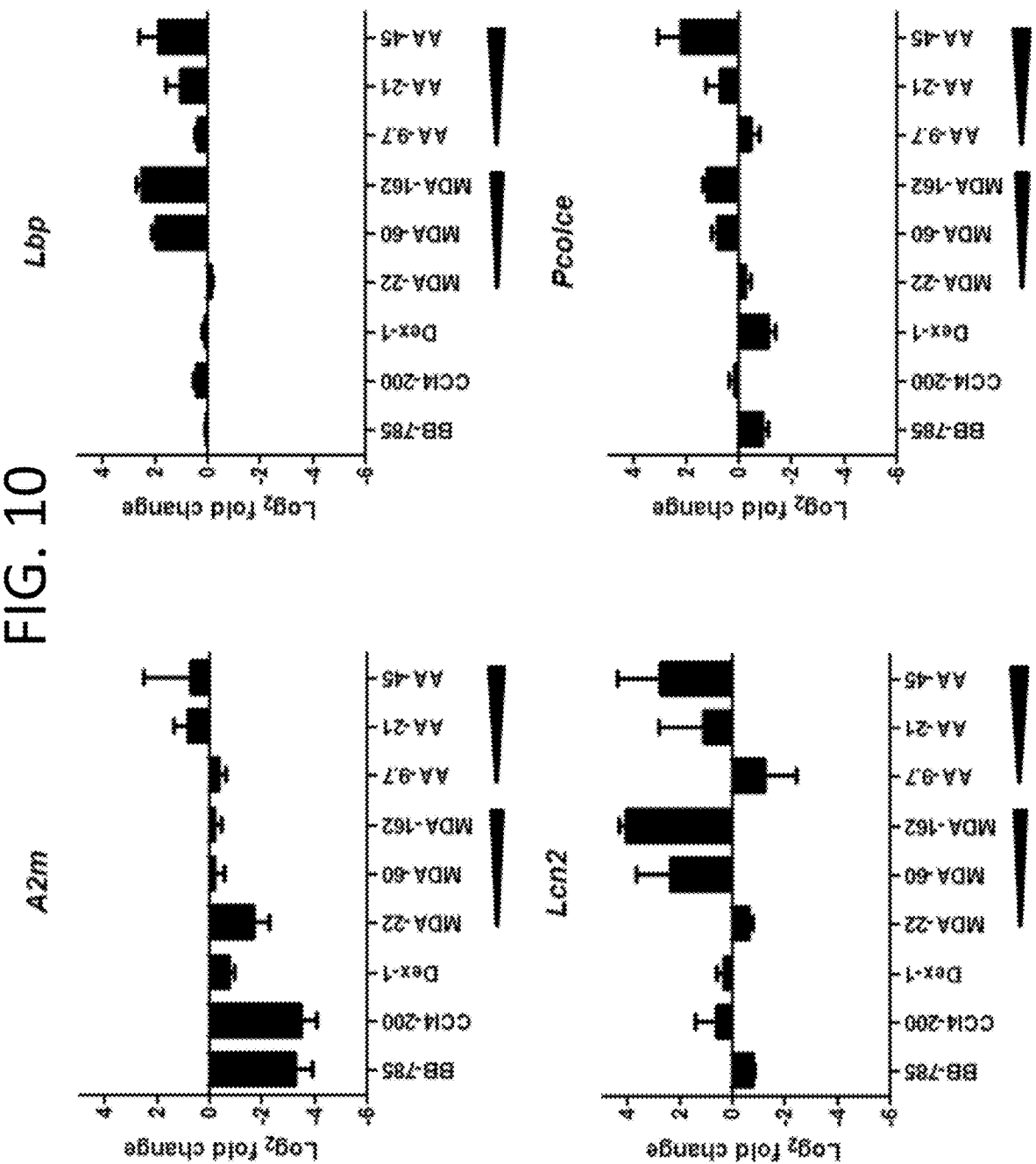
FIG. 10 exemplifies expression of four genes in a co-expression module containing A2m, an indicator on the FibroSure panel of biomarkers for steatohepatitis and liver fibrosis. Expression of four genes in a co-expression module associated with A2m was plotted in exposure groups segregated by chemical. Bromobenzene, carbon tetrachloride, and dexamethasone exposures correlated with histopathological evidence of vacuolation and/or glycogen accumulation. High-dose 4,4'-methylenedianiline and allyl alcohol exposures were associated with fibrosis histopathology without evidence of vacuolation. MDA, 4,4'-methylenedianiline; AA, allyl alcohol, BB, bromobenzene, CT, carbon tetrachloride; DEX, dexamethasone (doses in mg/kg).

Four of the genes included on the panel (Lcn2, A2m, Pcolce, and Lbp) were part of a co-expression module including A2m, the gene encoding a protein used in the Fibrosure test for fibrosis or steatohepatitis. These differentially expressed genes showed an expression pattern unique to the fibrosis phenotype and fibrogenic chemical classification (FIG. 10). Three of the genes (A2m, Lcn2, and Pcolce) were downregulated for bromobenzene (nonfibrogenic, vacuolation) relative to the other pathologies (Table 2). Pcolce expression levels induced by dexamethasone and bromobenzene (nonfibrogenic with lipid-associated pathologies) were anti-correlated with corresponding gene expression levels induced by 4,4'-methylenedianiline and allyl alcohol (fibrogenic compounds) (Table 3).

TABLE 3

Anti-correlated signature genes*

| Gene | Fibrogenic Mechanistic Category |
|---|---|
| Col1a1 | Fibrosis and ECM deposition/degradation |
| Col1a2 | Fibrosis and ECM deposition/degradation |
| Col4a1 | Fibrosis and ECM deposition/degradation |
| Cp | Inflammation/chemotaxis |
| Cyba | Xenobiotic metabolism |
| Fbn1 | Inflammation/chemotaxis |
| Itgal | Inflammation/chemotaxis |
| Itgb2 | Inflammation/chemotaxis |
| Lamac2 | Inflammation/chemotaxis |
| RT1-Da | Inflammation/chemotaxis |
| Pcolce | Fibrosis and ECM deposition/degradation |
| Plau | Fibrosis and ECM deposition/degradation |

Figure 11:
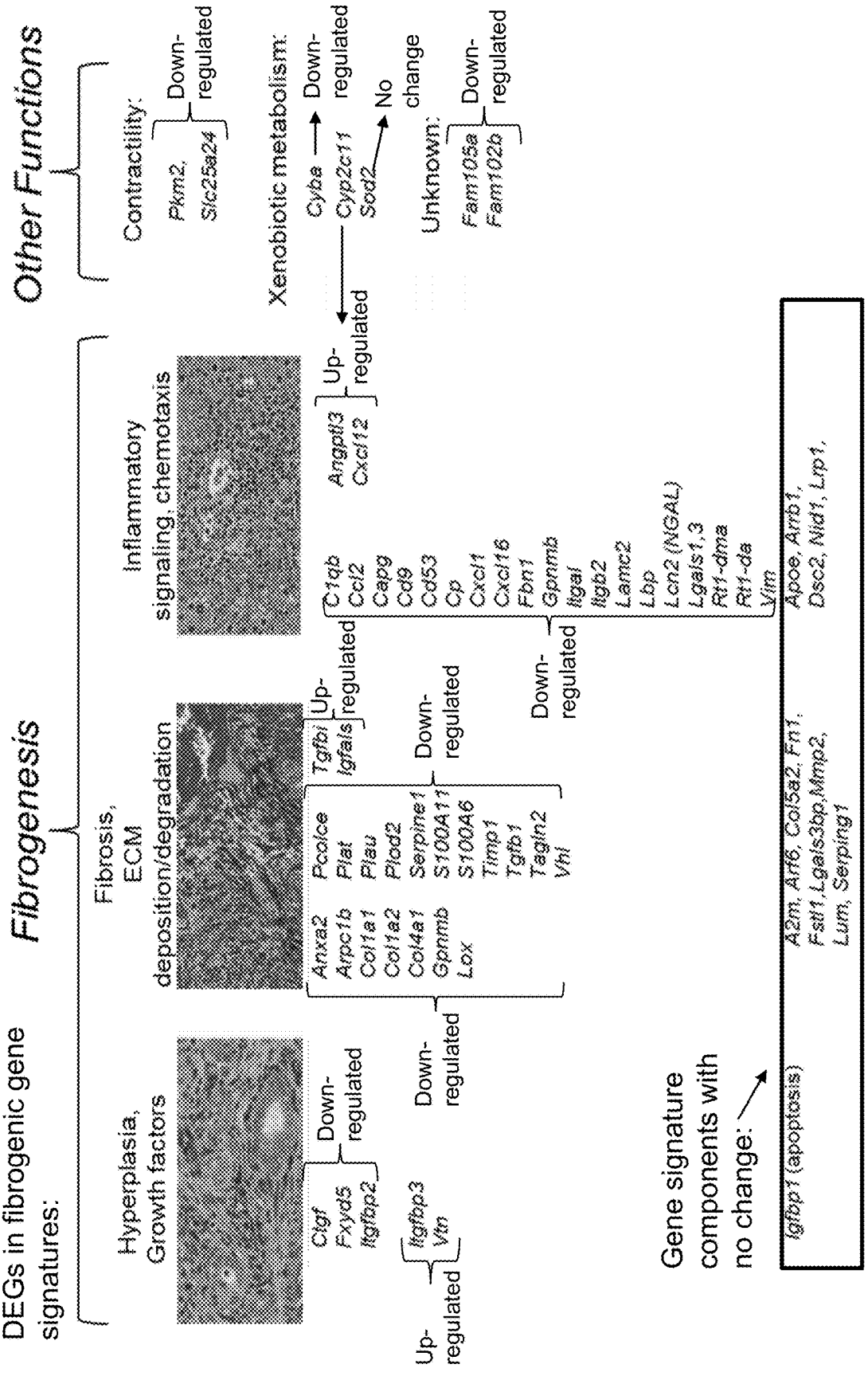
FIG. 11 exemplifies a summary of differentially expressed genes (DEGs) by putative classification in the fibrogenic gene signature panels. "Upregulated" indicates those genes that are expressed more than 1.5 times higher than under control conditions, and "downregulated" indicates those genes that are expressed more than 1.5 times lower than under control conditions, and "no change" indicates those genes that are expressed within 1.5 times higher than and 1.5 times lower than under control conditions from the heat-map in FIG. 8; ECM, extracellular matrix; *, results reported in the literature at later stages in disease progression with overt fibrosis and/or cirrhosis phenotypes.

*downregulated in nonfibrogenic chemicals and upregulated in fibrogenic chemicals with fibroplasia; ECM, extracellular matrix Differentially expressed genes in the fibrogenic signature gene panel were categorized into the following mechanistic groups based on a review of the literature for each gene: hyperplasia, fibrosis and extracellular matrix degradation, inflammatory signaling/chemotaxis, xenobiotic metabolism, and contractility (FIG. 11). Twelve genes upregulated above control expression by at least 1.5-fold in the fibrosis-inducing chemical-dose groups showed the opposite expression pattern in the non-fibrogenic chemical-dose groups (Table 2 and FIGS. 8 and 10). These genes were associated with multiple mechanistic categories of fibrosis, including inflammation and chemotaxis, extracellular matrix deposition/degradation, xenobiotic metabolism (FIG. 11). None of the anti-correlated genes associated with hyperplasia or contractility (FIG. 11; Table 3).

The human orthologs of the rodent genes are presented below in Table 4.

TABLE 4

Rat genes included in the diagnostic test for fibrosis, and human orthologs thereof

| | | Rat | | Human ortholog | |
|---|---|---|---|---|---|
| No. | Name | Gene symbol | Gene Id | Gene symbol | Gene Id |
| 1 | alpha-2-macroglobulin | A2m | 24153 | A2M | 2 |
| 2 | angiopoietin-like 3 | Angptl3 | 502970 | ANGPTL3 | 27329 |
| 3 | annexin A2 | Anxa2 | 56611 | ANXA2 | 302 |
| 4 | apolipoprotein E | Apoe | 25728 | APOE | 348 |
| 5 | ADP-ribosylation factor 6 | Arf6 | 79121 | ARF6 | 382 |
| 6 | actin related protein 2/3 com | Arpc1b | 54227 | ARPC1B | 10095 |
| 7 | arrestin, beta 1 | Arrb1 | 25387 | ARRB1 | 408 |
| 8 | complement component 1, q | C1qb | 29687 | C1QB | 713 |
| 9 | capping protein (actin filamen | Capg | 297339 | CAPG | 822 |
| 10 | chemokine (C-C motif) ligan | Ccl2 | 24770 | CCL2 | 6347 |
| 11 | Cd53 molecule | Cd53 | 24251 | CD53 | 963 |
| 12 | CD9 molecule | Cd9 | 24936 | CD9 | 928 |
| 13 | collagen, type I, alpha 1 | Col1a1 | 29393 | COL1A1 | 1277 |
| 14 | collagen, type I, alpha 2 | Col1a2 | 84352 | COL1A2 | 1278 |
| 15 | collagen, type IV, alpha 1 | Col4a1 | 290905 | COL4A1 | 1282 |
| 16 | collagen, type V, alpha 2 | Col5a2 | 85250 | COL5A2 | 1290 |
| 17 | ceruloplasmin (ferroxidase) | Cp | 24268 | CP | 1356 |
| 18 | connective tissue growth fac | Ctgf | 64032 | CTGF | 1490 |
| 19 | chemokine (C—X—C motif) liga | Cxcl1 | 81503 | CXCL1, CXCL3 | 2919, 292 |
| 20 | chemokine (C—X—C motif) liga | Cxcl12 | 24772 | CXCL12 | 6387 |
| 21 | chemokine (C—X—C motif) liga | Cxcl16 | 497942 | CXCL16 | 58191 |
| 22 | cytochrome b-245, alpha pol. | Cyba | 79129 | CYBA | 1535 |
| 23 | cytochrome P450, subfamily | Cyp2c11 | 29277 | CYP2C18 | 1562 |
| 24 | desmocollin 2 | Dsc2 | 291760 | DSC2 | 1824 |
| 25 | family with sequence similar | Fam102b | 365903 | FAM102B | 284611 |
| 26 | family with sequence similar | Fam105a | 310190 | FAM105A | 54491 |
| 27 | fibrillin 1 | Fbn1 | 83727 | FBN1 | 2200 |
| 28 | fibronectin 1 | Fn1 | 25661 | FN1 | 2335 |
| 29 | follistatin-like 1 | Fstl1 | 79210 | FSTL1 | 11167 |
| 30 | FXYD domain-containing ion | Fxyd5 | 60338 | FXYD5 | 53827 |
| 31 | glycoprotein (transmembran | Gpnmb | 113955 | GPNMB | 10457 |
| 32 | insulin-like growth factor bind | Igfals | 79438 | IGFALS | 3483 |
| 33 | insulin-like growth factor bind | Igfbp1 | 25685 | IGFBP1 | 3484 |
| 34 | insulin-like growth factor bind | Igfbp2 | 25662 | IGFBP2 | 3485 |
| 35 | insulin-like growth factor bind | Igfbp3 | 24484 | IGFBP3 | 3486 |
| 36 | integrin, alpha L | Itgal | 308995 | ITGAL | 3683 |
| 37 | integrin, beta 2 | Rgb2 | 309684 | ITGB2 | 3689 |
| 38 | laminin, gamma 2 | Lamc2 | 192362 | LAMC2 | 3918 |
| 39 | lipopolysaccharide binding p | Lbp | 29469 | LBP | 3929 |
| 40 | lipocalin 2 | Lcn2 | 170496 | LCN2 | 3934 |
| 41 | lectin, galactoside-binding, s | Lgals1 | 56646 | LGALS1 | 3656 |
| 42 | lectin, galactoside-binding, s | Lgals3 | 83781 | LGALS3 | 3958 |
| 43 | lectin, galactoside-binding, s | Lgals3bp | 245955 | LGALS3BP | 3959 |
| 44 | lysyl oxidase | Lox | 24914 | LOX | 4015 |
| 45 | low density lipoprotein recep | Lrp1 | 299858 | LRP1 | 11;I |
| 46 | lumican | Lum | 81682 | LUM | 4060 |
| 47 | matrix metallopeptidase 2 | Mmp2 | 81686 | MMP2 | 4313 |
| 48 | nidogen 1 | Nid1 | 25494 | NID1 | 4811 |
| 49 | procollagen C-endopeptidase | Pcolce | 29569 | PCOLCE | 5118 |
| 50 | pyruvate kinase, muscle | Pkm | 25630 | PKM | 5315 |
| 51 | plasminogen activator, tissue | Plat | 25692 | PLAT | 5327 |
| 52 | plasminogen activator, urokin | Plau | 25619 | PLAU | 5328 |
| 53 | procollagen lysine, 2-oxoglut | Plod2 | 300901 | PLOD2 | 5352 |

TABLE 4-continued

Rat genes included in the diagnostic test for fibrosis, and human orthologs thereof

| | Rat | | | Human ortholog | |
|---|---|---|---|---|---|
| No. | Name | Gene symbol | Gene Id | Gene symbol | Gene Id |
| 54 | RT1 class II, locus Da | RT1-Da | 294269 | HLA-DRA | 3122 |
| 55 | RT1 class II, locus DMa | RT1-DMa | 294274 | HLA-DMA | 3108 |
| 56 | S100 calcium binding protein | S100a11 | 445415 | S100A11 | 6282 |
| 57 | S100 calcium binding protein | S100a6 | 85247 | S100A6 | 6277 |
| 58 | serpin peptidase inhibitor, cla | Serpine1 | 24617 | SERPINE1 | 5054 |
| 59 | serpin peptidase inhibitor, cla | Serping1 | 295703 | SERPING1 | 710 |
| 60 | solute carrier family 25 (mito | Slc25a24 | 310791 | SLC25A24 | 29957 |
| 61 | superoxide dismutase 2, mit | Sod2 | 24787 | SOD2 | 6648 |
| 62 | transgelin 2 | Tagln2 | 304983 | TAGLN2 | 8407 |
| 63 | transforming growth factor, b | Tgfbl | 116487 | TGFBI | 7045 |
| 64 | TIMP metallopeptidase inhibi | Timp1 | 115510 | TIMP1 | 7076 |
| 65 | von Hippel-Lindau tumor sup | Vhl | 24874 | VHLL | 391104 |
| 66 | vimentin | Vim | 81818 | VIM | 7431 |
| 67 | vitronectin | Vtn | 29169 | VTN | 7448 |

Classifier for Predicting Fibrosis Development

The gene panel tested in the Group 1 experimental animals was used as the training data set to build a classifier for predicting fibrosis. Only genes present in both microarray and Bioplex data sets were used to build the classifier (59 of 62 genes). Of the 77 available samples, 19 were classified as true positives and 58 were classified as true negatives by histopathology. The internal cross-validation estimate of error rate was 2.6 for the training data set (Table 5). Random forest was used to identify the top genes that contribute most to the classifier performance (Table 5; FIGS. 1A-1F). The random forest classifier was tested using the Bioplex data set. Of the 35 total animal exposures, 13 exposures produced fibrosis with a histopathology score greater than 2 (true positives) and 22 exposures produced no fibrosis by histopathology (true negatives). The accuracy of prediction was 88.6% (Table 5). Area under the receiver operator curve (ROC) was 0.88 for the test set of data. (Ippolito D L, et. al. Gene expression patterns associated with histopathology in toxic liver fibrosis. Tox Sci. 2015 Sep. 22. pii: kfv214)

TABLE 5

Random forest classifier model predictions: training (Group 1) and testing Group (2) sets of experimental animals and data

| | Sensitivity | Specificity | Accuracy | Kappa |
|---|---|---|---|---|
| Training (Microarray)* | 94.7 | 98.3 | 97.4 | 0.93 |
| Testing (Bioplex) | 69.2 | 100.0 | 88.6 | 0.74 |

*internal cross-validation (estimate of error rate): 2.6

Protein Expression in the Plasma

Figure 13B:
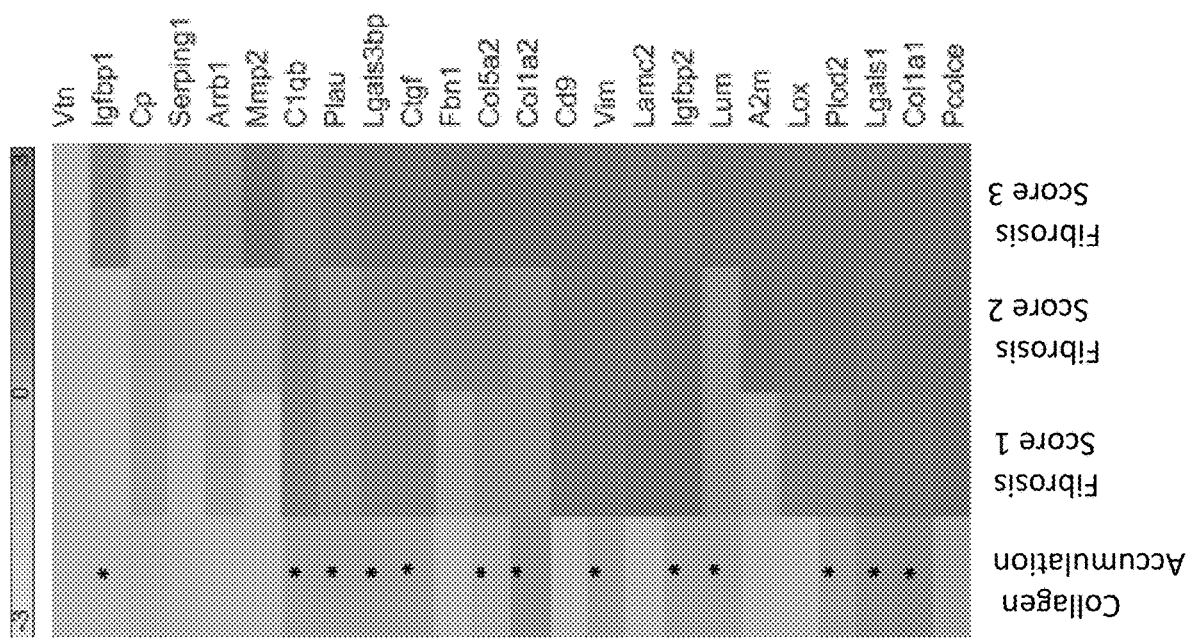
FIG. 13(B) exemplifies 24 genes associated with fibrosis, inflammation, and necrosis endpoints (Group 1 experimental animals) unique to the fibrosis endpoint alone identified by interference analysis (FDR<0.05 for necrosis, fibrosis, inflammation; ANOVA with contrasts). *, potential early indicators of fibrotic injury; genes differentially regulated in early fibrosis FIG. 14 exemplifies phenotypic anchoring of multiplexed gene, protein, and miRNA biomarker signatures in plasma to adverse outcome pathways of liver fibrosis
Figure 14:
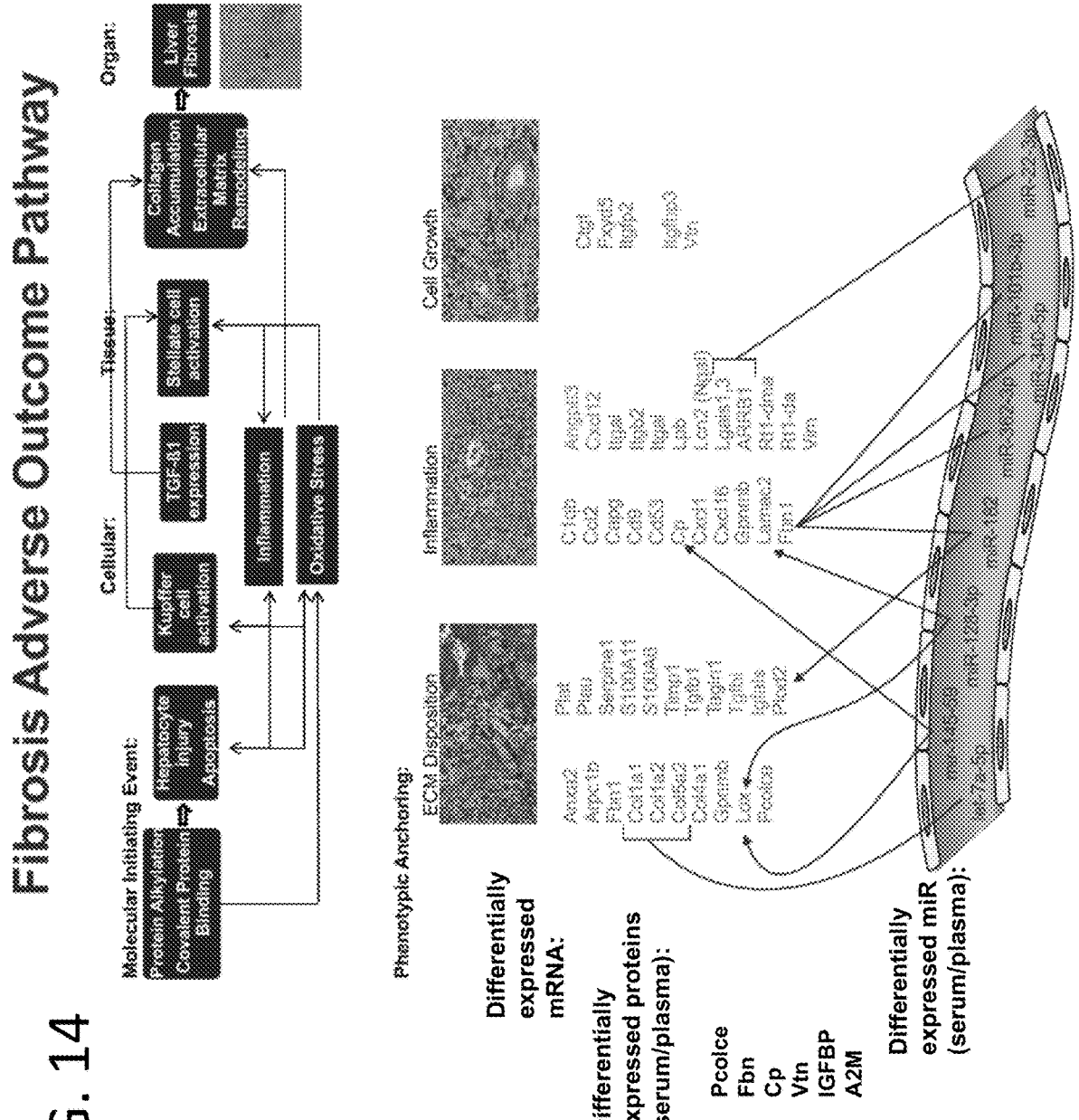

Four of the genes included on the panel (Lcn2, A2m, Pcolce, and Lbp) were part of a co-expression module including A2m, the gene encoding a protein used in the Fibrosure test for fibrosis or steatohepatitis (Rossi et al., 2003). The differentially expressed genes showed an expression pattern unique to the fibrosis phenotype and fibrogenic chemical classification (FIG. 13A). Pcolce was the most differentially expressed gene in the fibrosis cohorts (FIG. 13A). Pcolce expression levels induced by dexamethasone and bromobenzene were anti-correlated with corresponding gene expression levels induced by 4,4'-methylenedianiline and allyl alcohol (both fibrogenic compounds) (FIG. 13A). The protein product of Pcolce was significantly and dose-dependently upregulated in plasma in animals dosed with fibrogenic chemicals relative to non-fibrogenic chemicals (FIG. 13B). (Ippolito D L, et. al. Gene expression patterns associated with histopathology in toxic liver fibrosis. Tox Sci. 2015 Sep. 22. pii: kfv214)

Global semiquantitative proteomics analysis (iTRAQ analysis) identified protein products of a subset of the 24 genes differentially expressed in liver tissue specific for the fibrosis phenotype (Table 6). Six protein products were identified in plasma, four in the serum, and two in the liver tissue (Table 6). All protein products were identified in the contrast analysis as specific for the fibrosis phenotype. The direction of the changes in protein products matched the transcriptomics data with the exception of insulin-like growth factor binding protein complex acid labile subunit precursor. This protein was decreased in expression in plasma but the genes Igfbp1 and Igfbp2 were upregulated in liver tissue. (Ippolito D L, et. al. Gene expression patterns associated with histopathology in toxic liver fibrosis. Tox Sci. 2015 Sep. 22. pii: kfv214)

TABLE 6

Fold changes in tissue, plasma, or serum protein abundance measured by iTRAQ mass spectrometry (Group 2)

| | Protein* | GI # | p** | Fold change*** |
|---|---|---|---|---|
| Plasma: | fibronectin precursor | 186972114 | <0.0001 | −1.3 |
| | ceruloplasmin isoform 1 precursor | 401461786 | <0.0001 | 2.5 |
| | vitronectin precursor | 162287178 | <0.0001 | −1.6 |
| | insulin-like growth factor-binding protein complex acid labile subunit precursor | 71896592 | <0.0001 | −1.4 |

TABLE 6-continued

Fold changes in tissue, plasma, or serum protein abundance measured by iTRAQ mass spectrometry (Group 2)

|  | Protein* | GI # | p** | Fold change*** |
|---|---|---|---|---|
|  | alpha-2-macroglobulin precursor | 158138551 | 0.0370 | 2.2 |
| Serum: | vitronectin precursor | 162287178 | 1.0000 | −1.1 |
|  | ceruloplasmin isoform 1 precursor | 401461786 | <0.0001 | 2.4 |
|  | alpha-2-macroglobulin precursor | 158138551 | <0.0001 | 2.4 |
|  | complement C1q subcomponent subunit B precursor | 9506433 | 0.5700 | 1.6 |
| Tissue: | fibronectin precursor | 186972114 | <0.0001 | 1.4 |
|  | ceruloplasmin isoform 1 precursor | 401461786 | <0.0001 | 3.0 |

*Rattus norvegicus;
**p: p-value, Kruskal Wallis Analysis of Variance by Ranks;
***fold change (4,4'-methylenedianiline/vehicle)

Categorization of Fibrogenic Signature Gene Panel

Differentially expressed genes in the fibrogenic signature gene panel were categorized into the following mechanistic groups based on a review of the literature for each gene: hyperplasia, fibrosis and extracellular matrix degradation, inflammatory signaling/chemotaxis, xenobiotic metabolism, and contractility (FIGS. 13A and 13B). Twelve genes upregulated above control expression by at least 1.5-fold in the fibrosis-inducing compound-dose groups showed the opposite expression pattern in the non-fibrogenic compound-dose groups (Group 2 Bioplex experimental animals; FIGS. 13A and 13B). These genes were associated with multiple mechanistic categories of fibrosis, including inflammation and chemotaxis, and extracellular matrix deposition/degradation (FIGS. 13A and 13B). None of the anti-correlated genes were associated with hyperplasia or contractility (FIGS. 13A and 13B). (Ippolito D L, et. al. Gene expression patterns associated with histopathology in toxic liver fibrosis. Tox Sci. 2015 Sep. 22. pii: kfv214)

miRNA Expression in Serum Corroborates Transcription Data in Liver Tissue

Figure 12:
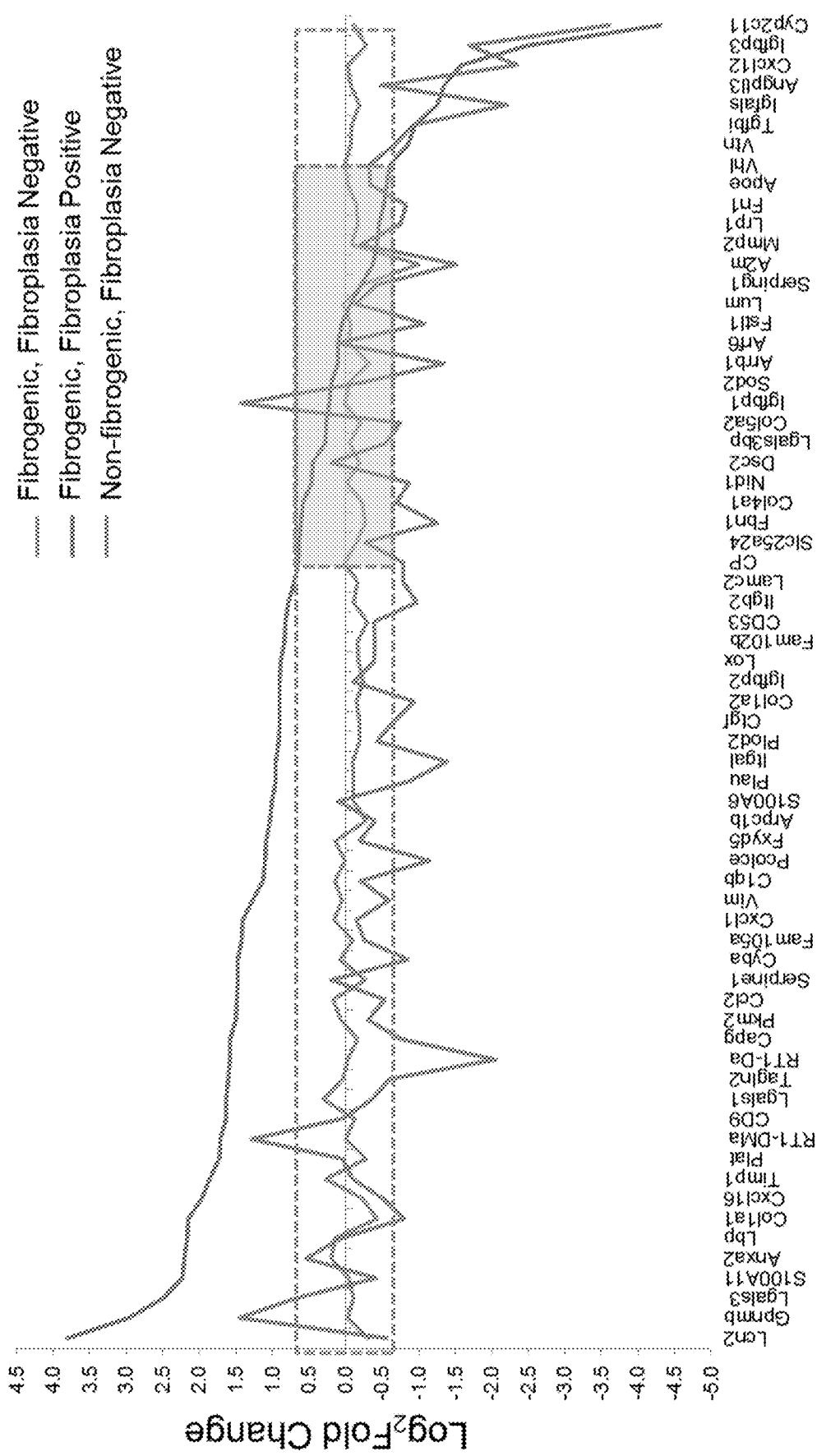
FIG. 12 exemplifies a differential gene signature pattern for rats treated with fibrogenic compounds with histopathological evidence of fibrosis. Expression ($\log_2$ fold-change over vehicle control) for 67 signature fibrogenic genes were plotted in decreasing level of $\log_2$ fold-change in the fibroplasia positive samples. The genes within the unshaded dashed box on the left represent genes unregulated in the fibroplasia positive sample relative to the controls. The genes within the shaded dashed box represent genes where a non-significant level of differential expression was found relative to the controls. The genes within the shaded dashed box on the right represent genes downregulated in the fibroplasia positive sample relative to the controls.

Serum miRNA expression was measured by next-generation sequencing. Gene expression in the liver was determined by microarray, and global serum and liver protein expression was determined by semi-quantitative mass spectrometry. We identified 16 differentially expressed miRNA in 4,4'-MDA-treated rats (12 upregulated, including miR-182, miR-122-5p, and -3p; 4 downregulated, including miR-340-5p and miR-182; FDR<0.05; FIG. 12). Transcriptomic analysis identified 506 differentially expressed genes in the liver. 13 miRNAs were predicted to target 100 unique differentially expressed genes in the liver. Global proteomics analysis identified 131 differentially expressed proteins in the liver and 53 in the serum. Of these, 7 miRNAs targeted 13 unique genes coding for differentially expressed liver tissue proteins and 3 miRNAs targeted 3 unique genes coding for serum proteins. These 16 differentially expressed miRNAs in the serum are predicted to target and potentially regulate gene expression contributing to the progression of toxic liver injury. (Fermenter M G et al. Serum miRNA as prognostic indicators of toxic liver injury. Submitted abstract in October 2015 for presentation at the Society of Toxicology in March 2016 (New Orleans, La.)).

REFERENCES

1. Ihmels J, Friedlander G, Bergmann S, et al. Revealing modular organization in the yeast transcriptional network. Nature genetics 2002; 31(4):370-377
2. AbdulHameed M. D. M., Tawa G J, Kumar K, et al. Systems level analysis and identification of pathways and networks associated with liver fibrosis. Plos One 2014; in press
3. Tawa G J, M. D. M. A, Yu X, et al. Characterization of chemically induced liver injuries using gene co-expression modules. Plos One 2014; in press
4. Dalmas D A, Scicchitano M S, Mullins D, et al. Potential candidate genomic biomarkers of drug induced vascular injury in the rat. Toxicol Appl Pharmacol 2011; 257(2):284-300
5. Gentleman R C, Carey V J, Bates D M, et al. Bioconductor: open software development for computational biology and bioinformatics. Genome biology 2004; 5(10):R80
6. Breitling R, Armengaud P, Amtmann A, Herzyk P. Rank products: a simple, yet powerful, new method to detect differentially regulated genes in replicated microarray experiments. FEBS letters 2004; 573(1-3):83-92
7. Yu H Y, Wang B L, Zhao J, et al. Protective effect of bicyclol on tetracycline-induced fatty liver in mice. Toxicology 2009; 261(3):112-118
8. Alcaraz N, Friedrich T, Kotzing T, et al. Efficient key pathway mining: combining networks and OMICS data. Integrative biology: quantitative biosciences from nano to macro 2012; 4(7):756-764
9. Vandesompele J, De Preter K, Pattyn F, et al. Accurate normalization of real-time quantitative RT-PCR data by geometric averaging of multiple internal control genes. Genome biology 2002; 3(7):RESEARCH0034
10. Joliffe I T, Morgan B J. Principal component analysis and exploratory factor analysis. Statistical methods in medical research 1992; 1(1):69-95
11. Ganter B, Tugendreich S, Pearson C I, et al. Development of a large-scale chemogenomics database to improve drug candidate selection and to understand mechanisms of chemical toxicity and action. Journal of biotechnology 2005; 119(3):219-244
12. Irwin R D. NTP Technical Report on the comparative toxicity studies of allyl acetate (CAS No. 591-87-7), allyl alcohol (CAS No. 107-18-6) and acrolein (CAS No. 107-02-8) administered by gavage to F344/N rats and B6C3F1 mice. Toxicity report series 2006(48):1-73, A71-H10
13. National Toxicology P. 4,4'-Methylenedianiline and its dihydrochloride salt. Report on carcinogens: carcinogen profiles/US Dept of Health and Human Services, Public Health Service, National Toxicology Program 2002; 10:152-153
14. National Toxicology P. Carbon tetrachloride. Report on carcinogens: carcinogen profiles/US Dept of Health and Human Services, Public Health Service, National Toxicology Program 2011; 12:86-89
15. Smialowicz R J, Simmons J E, Luebke R W, Allis J W. Immunotoxicologic assessment of subacute exposure of rats to carbon tetrachloride with comparison to hepatotoxicity and nephrotoxicity. Fundamental and applied toxicology: official journal of the Society of Toxicology 1991; 17(1):186-196
16. Institute of Laboratory Animal Resources. Guide for the Care and Use of Laboratory Animals. Washington, D.C.; 2011
17. Thoolen B, Maronpot R R, Harada T, et al. Proliferative and nonproliferative lesions of the rat and mouse hepatobiliary system. Toxicologic pathology 2010; 38(7 Suppl):5S-81S 18. Rossi E, Adams L, Prins A, et al. Validation of the FibroTest biochemical markers score in assessing liver fibrosis in hepatitis C patients. Clinical chemistry 2003; 49 (3):450-454
19. Ippolito D L, AbdulHameed M D, Tawa G J, Baer C E, Permenter M G, McDyre B C, Dennis W E, Boyle M H, Hobbs C A, Streicker M A, Snowden B S, Lewis J A, Wallqvist A, Stallings J D. Gene expression patterns associated with histopathology in toxic liver fibrosis. Tox Sci. 2015 Sep. 22. pii: kfv214. [Epub ahead of print]
20. Fermenter M G, McDyre B C, and Ippolito D L. Serum miRNA as prognostic indicators of toxic liver injury. Submitted abstract in October 2015 for presentation at the Society of Toxicology in March 2016 (New Orleans, La.).

The invention claimed is:

1. An array comprising a substrate and twenty-five or more first target oligonucleotides and no more than 74 target oligonucleotides in total, each first target oligonucleotide being immobilized on the substrate and specifically hybridizable to mRNA of, cDNA of, or miRNA against a different gene selected from the group consisting of Lcn2; Gpnmb; Lgals3; S100a11; Anxa2; Lbp; Col1a1; Cxcl16; Timp1; Plat; RT1-DMa; Cd9; Lgals1; Tagln2; RT1-Da; Capg; Pkm2; Ccl2; Serpine1; Serping1; Cyba; Fam105a; Cxcl1; Vim; C1qb; Pcolce; Fxyd5; Arpc1b; Pkm; S100a6; Plau; Itgal; Plod2; Ctgf; Col1a2; Igfbp2; Lox; Dsc2; Fam102b; CD53; Itgb2; Lamc2; Cp; Slc25a24; Fbn1; Col4a1; Sod2; Cyp2c11; Igfbp3; Cxcl12; Angptl3; Igfals; Lrp1; Tgfb1; Vtn; Vhl; and mammalian orthologs thereof.

2. The array of claim 1, wherein the first target oligonucleotides are labelled with a detectable label.

3. The array of claim 1, wherein the first target oligonucleotides comprise cDNA-specific sequences that each comprise at least one nucleotide difference from corresponding genomic DNA.

4. The array of claim 2, wherein the detectable label is directly detectable.

5. The array of claim 2, wherein the detectable label comprises biotin.

6. The array of claim 5, wherein streptavidin-conjugated phycoerythrin (SAPE) is bound to the biotin.

7. The array of claim 1, wherein the first target oligonucleotide is immobilized on the substrate due to binding with a capture probe.

8. A kit for the diagnosis of liver disease, comprising the array according to claim 1.

9. A method comprising contacting a biological sample from a mammalian subject with the array of claim 1.

10. A method comprising contacting a biological sample from a mammalian subject with the array of claim 2.

11. A method comprising contacting a biological sample from a mammalian subject with the array of claim 3.

12. A method comprising contacting a biological sample from a mammalian subject with the array of claim 4.

13. A method comprising contacting a biological sample from a mammalian subject with the array of claim 5.

14. A method comprising contacting a biological sample from a mammalian subject with the array of claim 6.

15. A method comprising contacting a biological sample from a mammalian subject with the array of claim 7.

16. A method comprising contacting a biological sample from a subject suspected of having a liver disease with the array of claim 8.

17. The method of claim 9, wherein the biological sample comprises a cell.

18. The method of claim 10, wherein the biological sample comprises a cell.

19. The method of claim 9, wherein the biological sample comprises mRNA.

20. The method of claim 9, wherein the biological sample comprises cDNA.

* * * * *